US008415493B2

(12) United States Patent
Eddaoudi et al.

(10) Patent No.: US 8,415,493 B2
(45) Date of Patent: Apr. 9, 2013

(54) ZEOLITE-LIKE METAL ORGANIC FRAMEWORKS (ZMOFS): MODULAR APPROACH TO THE SYNTHESIS OF ORGANIC-INORGANIC HYBRID POROUS MATERIALS HAVING A ZEOLITE LIKE TOPOLOGY

(75) Inventors: Mohamed Eddaoudi, Tampa, FL (US); Yunling Liu, Tampa, FL (US)

(73) Assignee: University of South Florida, Tampa, FL (US)

( * ) Notice: Subject to any disclaimer, the term of this patent is extended or adjusted under 35 U.S.C. 154(b) by 1589 days.

(21) Appl. No.: 11/410,359

(22) Filed: Apr. 24, 2006

(65) Prior Publication Data

US 2006/0287190 A1 Dec. 21, 2006

Related U.S. Application Data

(60) Provisional application No. 60/673,928, filed on Apr. 22, 2005.

(51) Int. Cl.
*C07F 3/00* (2006.01)
*B01J 20/22* (2006.01)
*B32B 3/26* (2006.01)
(52) U.S. Cl. ........................ 556/132; 502/401; 428/304.4
(58) Field of Classification Search ........................ None
See application file for complete search history.

(56) References Cited

U.S. PATENT DOCUMENTS 5,648,508 A * 7/1997 Yaghi .................................. 556/9

FOREIGN PATENT DOCUMENTS

WO  WO 02/088148 A1  11/2002

OTHER PUBLICATIONS

Barszcz, Barbara et al., Crystal and molecular structures of eight-coordinate (CuN4O4) and six-coordinate (CuN4O2) Cu(II) complexes with 4-methyl-5-imidazole-carboxaldehyde or 1-benzyl-2-hydroxymethylimidazole, respectively Spectroscopic and potentiometric studies, 1999, Polyhedron, 18, pp. 3713-3721.*
Maji, Tapas Kumar et al., Porous lanthanide-organic framework with zeolite-like topology, Mar. 24, 2005, Chem. commun., pp. 2436-2438.*
Gomez-Lor, B. et al., Novel 2D and 3D Indium Metal-Organic Frameworks: Topology and Catakytic Properties, Apr. 15, 2005, Chem. Mater., 14, pp. 2568-2573.*
Maji, Tapas et al., Porous lanthanide-organic framework with zeolite-like topology: electronic supplementary information, Mar. 2005, Chem. Commun., pp. 2436-2438.*
Caulder, D .L. et al. "Supermolecules by Design", *Acc. Chem. Res.*, 1999, pp. 975-982, vol. 32, No. 11.
Cheetham, A. K. et al. *Angew. Chem., Int. Ed.*, 1999, p. 3268-3292, vol. 38.

(Continued)

*Primary Examiner* — Melvin C Mayes
*Assistant Examiner* — Bijay Saha
(74) *Attorney, Agent, or Firm* — Saliwanchik, Lloyd & Eisenschenk

(57) ABSTRACT

The subject invention pertains to metal organic frameworks (MOF) having zeolite-net-like topology, their methods of use, and their modes of synthesis. The ZMOFs are produced by combining predesigned tetrahedral building, generated in situ using heterochelation, with polyfunctional ligands that have the commensurate angle and the required donor groups for the chelation. Each molecular building block is contrasted of a single metal ion and ligands with both heterochelation functionality and bridging functionality. Advantageously, zeolite-net-like MOFs of the subject invention are porous and contain large functional cavities, which is useful for encapsulating large molecules.

29 Claims, 17 Drawing Sheets
(10 of 17 Drawing Sheet(s) Filed in Color)

OTHER PUBLICATIONS

Chui, S. S.-Y. et al. "A Chemically Functionalizable Nanoporous Material [Cu$_3$(TMA)$_2$(H$_2$O)$_3$]$_n$", *Science*, Feb. 19, 1999, p. 1148-1150, vol. 283.

Corma, A. et al. "Issues in the Synthesis of Crystalline Molecular Sieves: Towards the Crystallization of Low Framework Density Structures", *ChemPhysChem.*, 2004, pp. 304-313, vol. 5, No. 3. Abstract Only.

Davis, M. E. "The Quest for Extra-Large Pore, Crystalline Molecular Sieves" *Chem-Eur. J.*, 1997, p. 1745-1750, vol. 3, No. 11. Abstract Only.

Davis, M. E. "New Vistas in Zeolite and Molecular Sieve Catalysis", *Acc. Chem. Res.*, 1993, pp. 111-115, vol. 26.

Davis, M. E. "Ordered Porous Materials for Emerging Applications", *Nature*, Jun. 20, 2002, pp. 813-821, vol. 417.

Desiraju, G. R. "Chemistry Beyond the Molecule", *Nature*, Jul. 26, 2001, pp. 397-400, vol. 412.

Eddaoudi, M. et al. "Modular Chemistry: Secondary Building Units as a Basis for the Design of Highly Porous and Robust Metal-Organic Carboxylate Frameworks", *Acc. Chem. Res.*, 2001, p. 319-330, vol. 34.

Evans, O. R. et al. "Crystal Engineering of NLO Materials Based on Metal-Organic Coordination Networks", *Acc. Chem. Res.*, 2002, pp. 511-522, vol. 35.

Hoskins, B. F. et al. "Design and Construction of a New Class of Scaffolding-like Materials Comprising Infinite Polymeric Frameworks of 3D-Linked Molecular Rods. A Reappraisal of the Zn(Cn)$_2$ and Cd(CN)$_2$ Structures and the Synthesis and Structure of the Diamond-Related Frameworks [N(CH$_3$)$_4$][Cu$^I$Zn$^{II}$(CN)$_4$] and Cu$^I$[4,4',4'',4'''-tetracyanotetraphenylmethane]BF$_4$·x C$_6$H$_5$NO$_2$", *J. Am. Chem. Soc.*, 1990, p. 1546-1554, vol. 112.

Jones, C. W. et al. "Organic-Functionalized Molecular Sieves as Shape-Selective Catalysts", *Nature*, May 7, 1998, pp. 52-54, vol. 393.

Kitagawa, S. et al. "Functional Porous Coordination Polymers" *Angew. Chem., Int. Ed.*, 2004, p. 2334-2375, vol. 43.

Li, H. et al. "Design and Synthesis of an Exceptionally Stable and Highly Porous Metal-Organic Framework", *Nature*, Nov. 18, 1999, pp. 276-279, vol. 402.

Moulton, B. et al. "From Molecules to Crystal Engineering: Supramolecular Isomerism and Polymorphism in Network Solids", *Chem. Rev.*, 2001, p. 1629-1658, vol. 101.

O'Keeffe, M. et al. "Frameworks for Extended Solids: Geometrical Design Principles", *J. Solid State Chem.*, 2000, pp. 3-20, vol. 152.

O'Keeffe, M. et al. "Unimodal 4-Connected 3D Nets. I. Nets Without 3- or 4- Rings", *Acta Crystallogr.*, 1992, pp. 663-669, vol. A48.

Ozin, G. A. "Panoscopic Materials: Synthesis Over 'All' Length Scales", *Chem. Comm.*, 2000, pp. 419-432.

Paillaud, J. L. et al. "Extra-Large-Pore Zeolites with Two-Dimensional Channels Formed by 14 and 12 Rings" *Science*, May 14, 2004, p. 990-992, vol. 304.

Seo, J. S. et al. "A Homochiral Metal-Organic Porous Material for Enantioselective Separation and Catalysis", *Nature*, Apr., 27, 2000, pp. 982-986, vol. 404.

Seidel, S. R. et al. "High-Symmetry Coordination Cages via Self-Assembly", *Acc. Chem. Res.*, 2002, pp. 972-983, vol. 35.

Stein, A. et al. "Turning Down the Heat: Design and Mechanism in Solid-State Synthesis", *Science*, Mar. 12, 1993, pp. 1558-1564, vol. 259, No. 5101.

Takeda, N. et al. "A Nanometre-Sized Hexahedral Coordination Capsule Assembled from 24 Components", *Nature*, Apr. 29, 1999, pp. 794-796, vol. 398.

Yaghi, O. M. et al. "Design of Solids from Molecular Building Blocks: Golden Opportunities for Solid State Chemistry",*J. Solid State Chem.*, 2000, pp. 1-2, vol. 152.

Yaghi, O. M. et al. "Reticular Synthesis and the Design of New Materials", *Nature*, Jun. 12, 2003, pp. 705-714, vol. 423.

Yamamoto, K. et al. *Science*, Apr. 18, 2003, p. 470-472, vol. 300.

Dybtsev D.N., et al., "Microporous Manganese Formate: A Simple Metal-Organic Porous Material with High Framework Stability and Highly Selective Gas Sorption Properties" J. Am. Chem. Soc., 2004, pp. 32-33, vol. 126.

Li H., et al., "Establishing Microporosity in Open Metal-Organic Frameworks: Gas Sorption Isotherms for Zn(BDC)" *J. Am. Chem. Soc.*, 1998, pp. 8571-8572, vol. 120.

Papaefstathiou G.S., et al., "Inverted Metal Organic Frameworks: Solid-State Hosts with modular Functionality" *Coordination Chemistry Reviews*, 2003, pp. 169-183, vol. 169, No. 14.

Qin, C. et al. "A series of three-dimensional lanthanide coordination polymers with rutile and unprecedented rutile-related topologies", *Inorganic Chemistry*, vol. 44, No. 10, Oct. 3, 2005, pp. 7122-7129.

Suarez, S. et al. "Lanthanide luminescent mesomorphic complexes with macrocycles derived from diaza-18-crown-6", *New Journal of Chemistry*, vol. 29, Oct. 2005, pp. 1323-1334.

Storr, T. et al. "Ru$^{III}$ complexes of edta and dtpa polyaminocarboxylate analogues and their use as nitric oxide scavengers", *European Journal of Inorganic Chemistry*, No. 13, Jul. 2005, pp. 2685-2697.

Liu, Y. et al. "4-Connected metal-organic assemblies mediated via heterochelation and bridging of single metal ions: Kagome lattice and the M$_6$L$_{12}$ octahedron", *Journal of the American Chemical Society*, vol. 127, No. 20, May 25, 2005, pp. 7266-7267.

Lin, Z. et al. "The indium-carboxylate chain structure with the rectangular tunnels", *Inorganic Chemistry Communications*, vol. 8, No. 2, Feb. 2005, pp. 199-201.

Xu, Y. et al. "Oxidation-state and coordination site specificity influencing dimensional extension and properties of two iron complexes with similar helical chains", *European Journal of Inorganic Chemistry*, No. 22, Nov. 2004, pp. 4457-4462.

Noro, S-I. et al. "Framework Control by a Metalloligand Having Multicoordination Ability: New Synthetic Approach for Crystal Structures and Magnetic Properties", *Inorganic Chemistry*, vol. 44, No. 1, 3 Dec. 2004, pp. 133-146.

Du, M. et al. "Hydrothermal synthesis, characterization and crystal structure of a three-dimensional (3D) Zn$^{II}$ supramolecular compound with ethylenediaminetetraacetic acid ligand and 4-(carboxylate)pyridinium guests", Journal of Molecular Structure, vol. 701, No. 1-3, Sep. 1, 2004, pp. 119-124.

Chen, B. et al. "Chloro[N,N'-ethylenebis(5-carboxysalicylideneiminato)]iron(III)", *ACTA Crystallographica. Section E: Structure Reports Online*, vol. 60, No. 6, Jun. 2004, pp. M732-M734.

Shi, X. et al. "Novel supramolecular frameworks self-assembled from one-dimensional polymeric coordination chains", *European Journal of Inorganic Chemistry*, No. 1, Jan. 2004, pp. 185-191.

Ma, C. et al. "Trans-Diaquabis(1H-imidazole-4,5-dicarboxylate-K$^2$N$^3$,Q$^4$)manganese(II)", Acta Crystallographica, Section C: Crystal Structure Communications, vol. 59, No. 12, Dec. 2003, pp. M516-M518.

Tian, Y-Q. et al. "$\{[In3(pzdc)_6]^3\}\infty$: A metal-organic framework of distorted NbO-like net (pzdc=pyrazine-2,3-dicarboxylato)", *Chemistry Letters*, vol. 32, No. 9, Sep. 2003, pp. 796-797.

Takahashi, M. et al. "Utilization of dendritic framework as a multivalent ligand: a functionalized gadolinium(III) carrier with glycoside cluster periphery", *Tetrahedron Letters*, vol. 41, No. 44, Oct. 28, 2000, pp. 8485-8488.

Polyakova, I.N. et al. "Crystal structure of cobalt(III) compound with ethylenediamine-N,N'-Di-3-propionic acid, [Co(H$_2$Eddp)(HEddp)]Br$_2$.4H20", *Crystallography Reports*, vol. 45, No. 2, Mar. 2000, pp. 222-226.

Ivanov, S.A. et al. "Mercury(II) Complexes of Iminodiacetic, Nitrilotriacetic, Ethylenediaminetetraacetic, and Diethylenetriaminepentaacetic Acids: Synthesis and Structure", *Russian Journal of Inorganic Chemistry*, vol. 43, No. 3, 1998, pp. 351-358.

Tian, Y.Q. et al. "[Co$_5$(im)$_{10}$·2MB]∞: A Metal-Organic Open Framework with Zeolite-Like Topology**" *Angew. Chem. Int. Ed.*, 2002, 41(8):1384-1386.

* cited by examiner

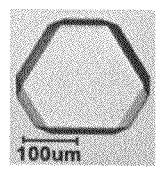
Fig. 6A
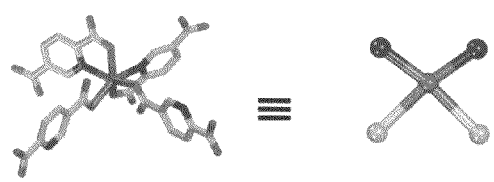
Fig. 6B
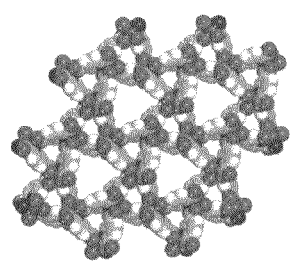     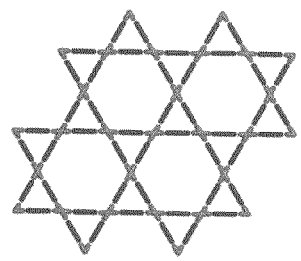
Fig. 6C               Fig. 6D 1H-Imidazole-2-carboxylic acid 1H-Imidazole-4,5-dicarboxylic acid 1H-Pyrrole-2,4-dicarboxylic acid 2,7-Diaza-anthracene-1,8-dicarboxylic acid Pyrimidine-4,6-dicarboxylic acid Pyridine-2,5-dicarboxylic acid 2,7-Diaza-anthracene-3,6-dicarboxylic acid Benzene-1,2,4,5-tetracarboxylic acid   Naphthalene-2,3,6,7-tetracarboxylic acid   Anthracene-2,3,6,7-tetracarboxylic acid

ZEOLITE-LIKE METAL ORGANIC FRAMEWORKS (ZMOFS): MODULAR APPROACH TO THE SYNTHESIS OF ORGANIC-INORGANIC HYBRID POROUS MATERIALS HAVING A ZEOLITE LIKE TOPOLOGY

CROSS-REFERENCE TO A RELATED APPLICATION

This application claims the benefit of U.S. Provisional Application Ser. No. 60/673,928, filed Apr. 22, 2005, which is hereby incorporated by reference herein in its entirety, including any figures, tables, and drawings.

BACKGROUND OF THE INVENTION

This invention relates to metal organic frameworks (MOFs) having zeolite-net-like topologies, their methods of design, their modes of synthesis, and their modes of use.

Synthetic solid-state materials play a critical role in our economy and everyday life. We are at a critical juncture where both improvement of existing materials and new approaches to the design of novel materials are required to address the many technological challenges that face us concerning the environment, biomedicine, pharmaceutical science, energy, space exploration, superconductors, microelectronics, photonics, supercomputers, super-catalysts, chiral separations and hydrogen storage for fuelling applications. (Ozin, 2000). In spite of great progress in the area of solid state materials that has afforded refined porous solids such as zeolites, (Davis, 2002), the basic synthetic approaches have remained unchanged for much of the twentieth century; discovery of new materials has largely been serendipitous, using standard methods (Stein, 1993).

Zeolites, purely inorganic microporous crystalline solids constructed from tetrahedral building units sharing corners, are an important class of solid-state materials and are of major economic significance owing to the homogeneously sized and shaped openings and voids (Davis M. E., 2004; Corma, A. and Davis, M. E., 2004). These confined spaces permit their conventional use par excellence as shape- and size-selective catalysts, ion exchangers and adsorbents. These properties are closely related to the framework's structural features such as the size of the pore openings and cavities. Difficulties in altering the zeolite i) structural features in order to enclose extra-large cavities beyond the 1 nm prison (Paillaud et al., 2004) and/or ii) composition to contain a periodic array of intra-framework organic functionality (Yamamoto, K., 1998; Jones, C. W. et al, 1998) have thus far restricted their application to small molecules. Rational construction of tetrahedrally connected porous materials, related in their topological properties to zeolites with extra-large cavities and periodic intra-framework organic functionality, is an ongoing synthetic challenge, and it is of exceptional scientific and technological interest, offering great potential for innovative applications pertaining to large molecules, nanotechnology, optics, sensor-technology, medicine, etc. (Davis, M. E., 1997).

Assembly of finite supramolecular polyhedra and periodic extended networks from molecular building blocks (MBBs) offers great potential for the rational design and synthesis of functional materials and nanostructures (Cheetham, A. K., et al., 1999; Yaghi, O. M., et al., 2003; Seo, J. S., et al., 2000; Desiraju, G. R., 2001). This approach has been explored and, to some extent, has proven to be successful in metal-ligand directed assembly (Moulton, B. and M. J. Zaworotko, 2001; Hoskins, B. F. and R. Robson, 1990; Stang, P. J. and S. R. Seidel, 2002; Takeda, N., et al., 1999; Kitagawa, S., R. Kitaura and S. Noro, 2004; Eddaoudi, M., et al., 2001; Caulder, D. L. and K. N. Raymond, 1999; Yaghi, O. M., et al., 2003). Metal-carboxylate based clusters, where metals are locked into their positions, have been synthesized in situ and successfully used as rigid directional secondary building emits to design and construct stabile open metal-organic assemblies that maintain their structural integrity even upon complete removal of their guest molecules (Li, H., M. Eddaoudi, M. O'Keeffe and O. M. Yaghi, 1999; Chui, S. S.-Y., et al., 1999; Yaghi, O. M et al., 2000; Yaghi, O. M., et al., 2003).

Although the number of topologies found in natural and synthetic inorganic zeolites, four-connected nets, is large (over 161 structures), prior attempts to construct ZMOFs from tetrahedral molecular building blocks and ditopic linkers have frequently lead to structures not related to zeolite topologies (mainly cubic diamond topology: Yaghi, O. M., et al, 2003). Zeolites, alumino-silicate networks, are purely inorganic microporous crystalline materials constructed from tetrahedral building blocks sharing corners, $[SiO_4]^{4-}$ and $[AlO_4]^{5-}$. The introduction of aluminum in the silicate lattice generates a negative charge on the zeolite framework. The resulting anionic framework charge is balanced by positively charged inorganic or organic cations. These cations, accessible through the pores, provide zeolites with their large ion-exchange capacity and their utility as size- or shape-selective catalysts (Davis, M. E., 1993). Extension of their use to other applications has been hindered by several difficulties in functionalizing and widening their pores without changing their overall topology (Davis, M. E., 2002). Their structure is based on tetrahedral building blocks linked together to form different cage types or channels.

Metal organic frameworks constructed from tetrahedral building units and having zeolite-net-like topologies are scarce; however, a dominant number of inorganic zeolites are constructed from tetrahedral building units. Attempts to construct MOFs with zeolite-like topology based on the assembly of such building units have constantly lead to the formation of a cubic diamond-like topology, regarded as the default structure for the assembly of extended 3-I frameworks from 4 connected nodes. The cubic diamond-like topology ($TX_2$) is considered the default structure for the assembly of simple tetrahedral building blocks. The cubic diamond structure is expected to form if the reaction involved simple tetrahedral building blocks, particularly single metal ions connected by flexible linkers (O'Keeffe, M., et al., 2000).

It has been shown that synthesis of open frameworks by assembly of single metal ions with di-, tri-, and poly-topic N-bound organic linkers such as 4,4'-bipyridine has produced many cationic framework structures and attempts to evacuate/exchange guests within the pores just about consistently resulted in a collapse of the host framework (Evans, O. et al., 2002). Also, the flexibility of the N-M-N angle in the tetrahedral building bock $MN_4$ does not permit their use as a neat directional secondary building unit to design and construct complex structures other than the default cubic diamond structure.

BRIEF SUMMARY OF THE INVENTION

The subject invention provides systematic synthetic pathways for the synthesis of porous crystalline solids containing covalently interacting components. In a preferred embodiment, the crystalline solids and metal organic frameworks exhibit zeolite-net-like topologies. The design and synthesis of robust metal-organic assemblies based on single metals as vertices is to render each heterocoordinated single metal, formed in situ, rigid and directional using, for example, nitrogen-oxygen chelates. The metal-nitrogen bonds will direct the topology, while the oxygen atoms will complete the coordination sphere of the metal ion and lock it into its position through the formation of rigid five-membered rings.

The subject invention provides pathways for the design and synthesis of MOFs with zeolite-net-like topologies having extra-large cavities.

The subject invention relates to methods for using the porous crystalline solids of the subject invention. In a preferred embodiment, methods of the subject invention are directed to methods of encapsulating, and/or including, large molecules, ion exchange, encapsulating prophyrin derivatives and their metalation.

The subject invention also pertains to methods for using rigid directional single-metal-ion building blocks, $MN_x(CO_2)_y$ (where M is a metal), for the design and synthesis of discrete and extended metal-organic assemblies generally and MOFs with zeolite-net-like topologies in particular.

BRIEF DESCRIPTION OF THE DRAWINGS

The patent or application file contains at least one drawing executed in color. Copies of this patent or patent application publication with color drawings will be provided by the Patent Office upon request and payment of the necessary fee.

FIG. 1A shows the eight-coordinated molecular building blocks (MBBs). Their formation is generated by the heterochelation of the metal with N— and O— donor groups, from 4 similar ligands, to form rigid five membered rings. The MBB, $MN_4(CO_2)_4$ where the M-N direct the topology and the carboxylates lock the metal into its position, can be regarded as a tetrahedral building unit $MN_4$ FIG. 1C. The polyfunctional ligand, imidazoledicarboxylate (ImDC) (FIG. 1B) having the nitrogen group at 145° bond angles, bridge the building units as shown in FIG. 1D. FIG. 1B shows imidazoledicarboxylate heterochelating the indium metal ion entity. The MBB $MN_4(CO_2)_4$ can viewed as a 4-connected tetrahedral secondary building units (SBUs) FIG. 1B. FIG. 1D shows a fragment of the rho-ZMOF structure constructed from the assembly α-cages linked together by the double 8-membered. FIG. 1F shows a the topological representation for rho-ZMOFs where the vertices represent the metal ions and the lines represent the ligands. FIG. 1D, the color green indicates In, the color gray indicates C, the color red indicates O and the color blue indicates N. Guest and hydrogen atoms are not shown for clarity. The large yellow spheres represent the largest sphere that would fit in the cavities without touching the van der Walls atoms of the framework.

FIG. 2A shows a GME cage in the USF-ZMOF. FIG. 2B shows the same GME cage as in FIG. 1F with the simplified tetrahedron knot. FIG. 2C shows the new cage in USF-ZMOFs. FIG. 2D shows the new cage in USF-ZMOFs with the simplified tetrahedron knot, composed of 32 indium atoms: ten 4-rings, four 6-rings, four 8-rings. FIG. 2E shows the framework of the USF-ZMOF viewed along a direction. FIG. 2F shows tiles of the USF-ZMOFs nets. The GME cage is shown in green. The new cage is shown in red. In atoms are represented by the color green. Carbon atoms are represented by the color gray. Oxygen atoms are represented by the color red. Nitrogen atoms are represented by the color blue. Guest and hydrogen atoms are not shown for clarity. A GME cage ($4^9 6^2 8^3$) is shown in FIG. 2B and new cage ($4^{10} 6^4 8^4$) is shown in FIG. 2C and their combination lead to USF-ZMOF shown in FIG. 2F.

The USF ZMOF coordination sequence is

| In1 | 4 | 9  | 18 | 32 | 48 | 67 | 93 | 123 | 154 | 190 | 234 | 282 | 329; |
| In2 | 4 | 9  | 18 | 31 | 47 | 69 | 96 | 125 | 156 | 192 | 235 | 282 | 331; |
| In3 | 4 | 10 | 18 | 30 | 50 | 72 | 92 | 120 | 158 | 198 | 234 | 276 | 330. | vertex symbol:

| In1 | 4 | 4 | 4 | 6 | 8 | 8;  |
| In2 | 4 | 4 | 4 | 6 | 8 | 8;. |
| In3 | 4 | 4 | 6 | 6 | 8 | 8.  |

Figure 3A:
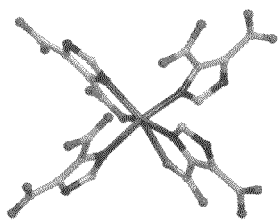
Figure 3B:
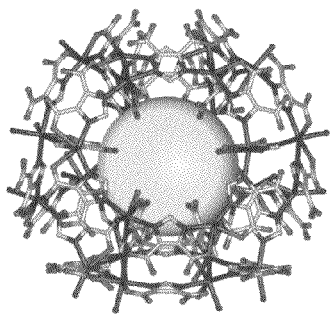
Figure 3C:
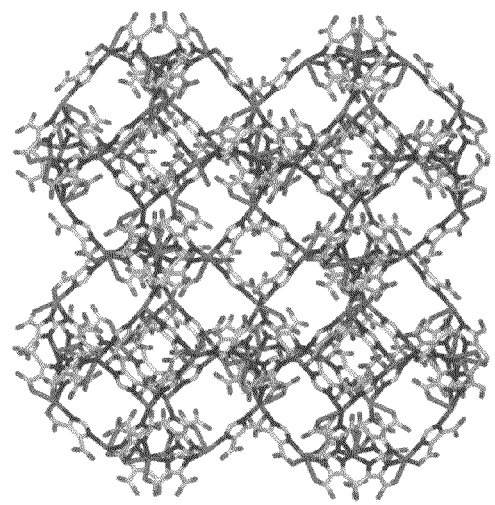
Figure 3D:
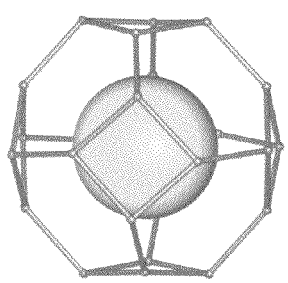
Figure 3E:
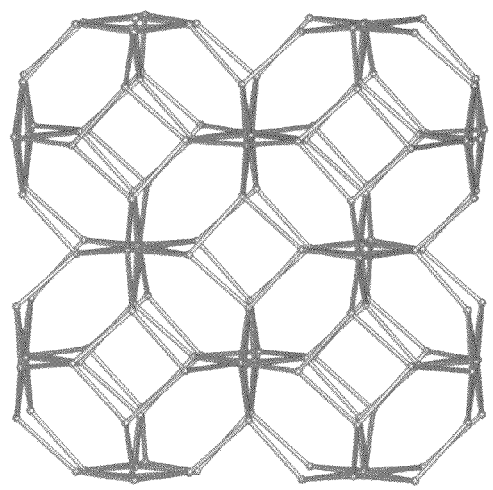

FIGS. 3A-3E shows single crystal structures of SOD-ZMOFs. FIG. 3A shows the 6-coordinated Indium centered secondary building units (SBUs). FIG. 3B shows a single SOD-cage. FIG. 3C shows the same SOD-cage with the simplified tetrahedron knot. FIG. 3D shows the stick view of the SOF-ZMOFs structure along a cube axis. FIG. 3E shows a perspective view of the SOF-ZMOFs structure along a cube axis. Indium atoms are represented by the color green. Carbon atoms are represented by the color gray. Oxygen atoms are represented by the color red. Nitrogen atoms are represented by the color blue. Guest and hydrogen atoms are not shown for clarity. The large yellow spheres represents the largest sphere that would fit in the cavities without touching the van der Walls atoms of the framework.

Figure 4A:
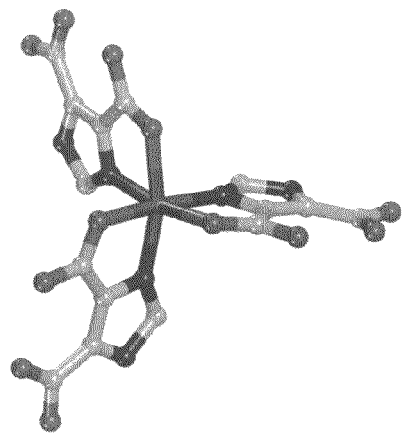
Figure 4B:
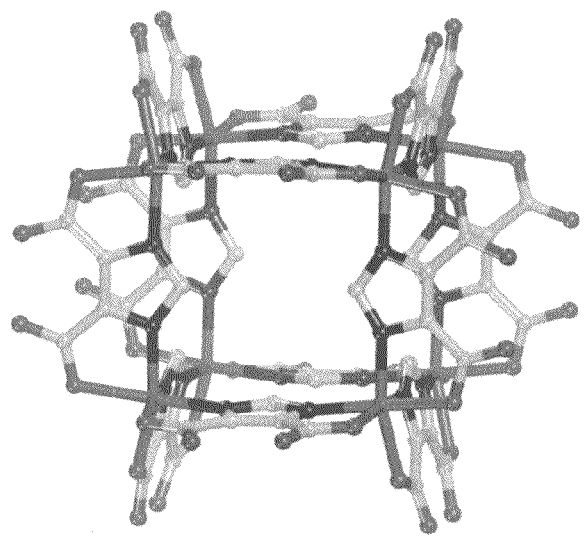

FIG. 4A shows the secondary building unit of $M(ImDC)_3$, a $MN_3O_3$ SBU. FIG. 4B shows the structure of the $[M_8(HImDC)_{12}]^{8-}$ cube.

Figure 5A:
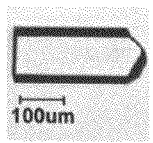
Figure 5B:
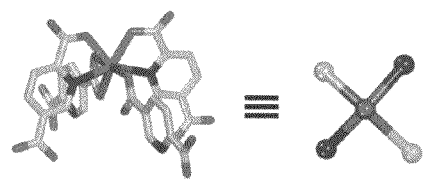
Figure 5C:
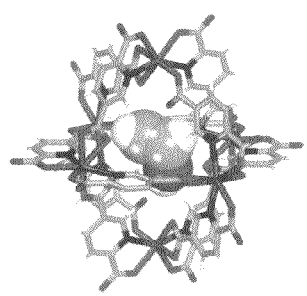
Figure 5D:
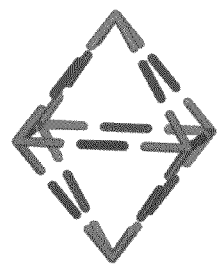
Figure 5E:
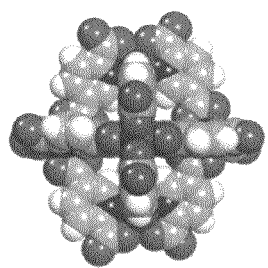
Figure 5F:
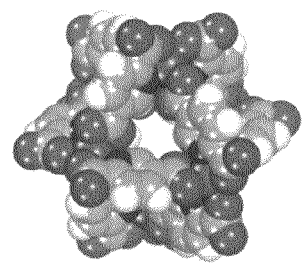

FIG. 5A shows an optical image of $In_6(2,5-PDC)_{12}(1,2-H_2DACH)_2(DMF)_5(EtOH)_5(H_3O)_2$. FIG. 5B shows the crystal structure of $In_6(2,5-PDC)_{12}(1,2-H_2DACH)_2(DMF)_5(EtOH)_5(H_3O)_2$. The trans pyramidal building unit is shown. FIG. 5C shows a view of the octahedron cage with one encapsulated ethanol molecule (space-filling model). FIG. 5D shows a schematic representation of the octahedron. FIG. 5E shows a space-filling view through a corner. FIG. 5F shows a space-filling view along the trigonal windows (color scheme: carbon=gray; hydrogen=white, nitrogen=blue, oxygen=red, and indium=green).

FIG. 6A shows an optical image of the X-ray crystal structure for homogenous microcrystalline $In(2,5-PDC)_2(HT-MDP)(EtOH)(H_2O)_2$. FIG. 6B shows an illustration of the indium molecular building block, $InN_2(CO_2)_4$, which can be viewed as a 4-connected node, cis-$InN_2(CO_2)_2$. FIG. 6C shows the space-filling representation of a 2-I Kagome layer (color scheme: carbon=gray, hydrogen=white, nitrogen=blue, oxygen=red, indium=green). FIG. 6D shows a schematic representation of the Kagome lattice.

Figure 7:
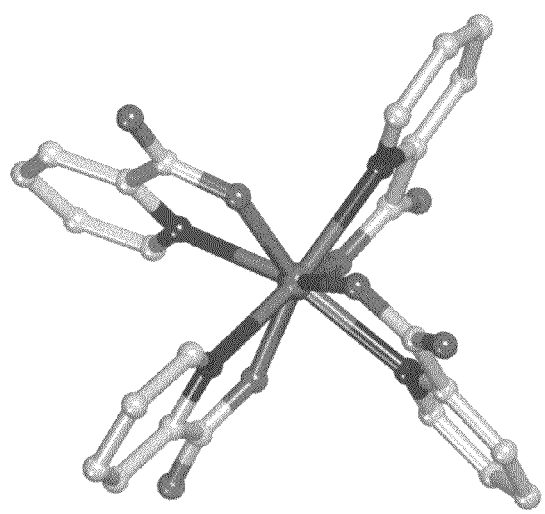

FIG. 7 shows the MBB for the metal cluster $MN_4O_4$ (color scheme: M=Green, N=Blue, O=Red).

Figure 8:
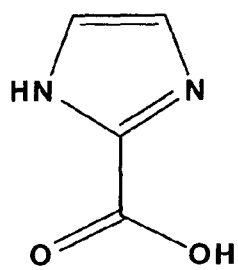
Figure 8:
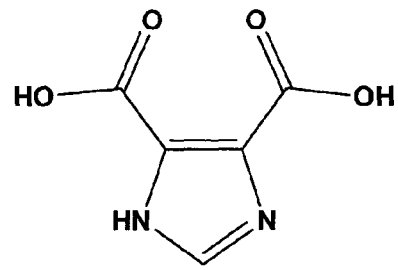
Figure 8:
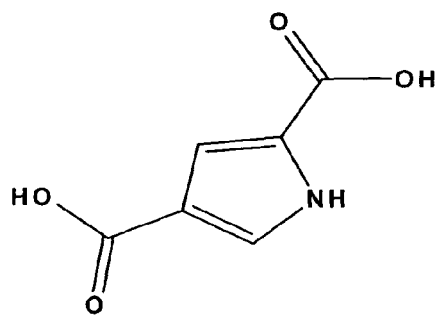
Figure 8:
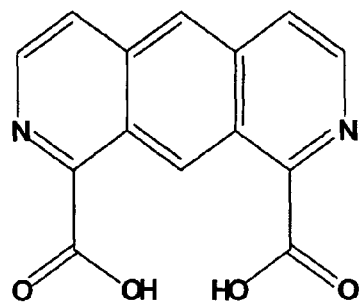
Figure 8:
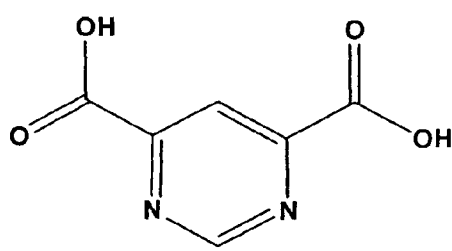
Figure 8:
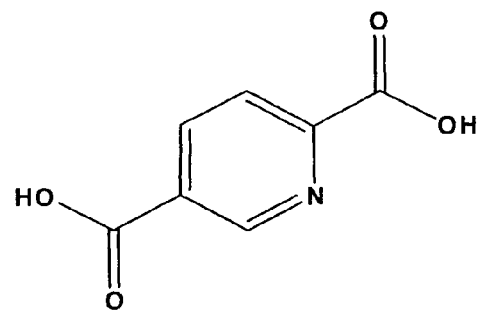
Figure 8:
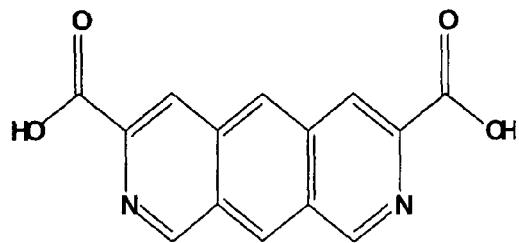

FIG. 8 shows several chemical structures for potential ligands useful for assembling into zeolite networks with combinations with MBBs of the subject invention.

Figure 9A:
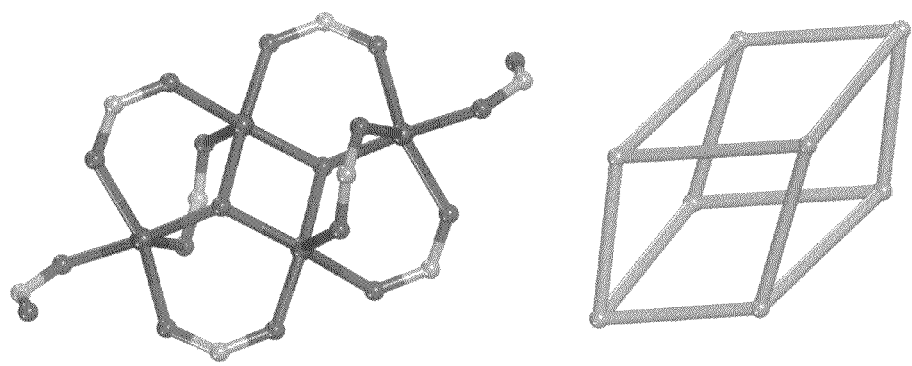
Figure 9B:
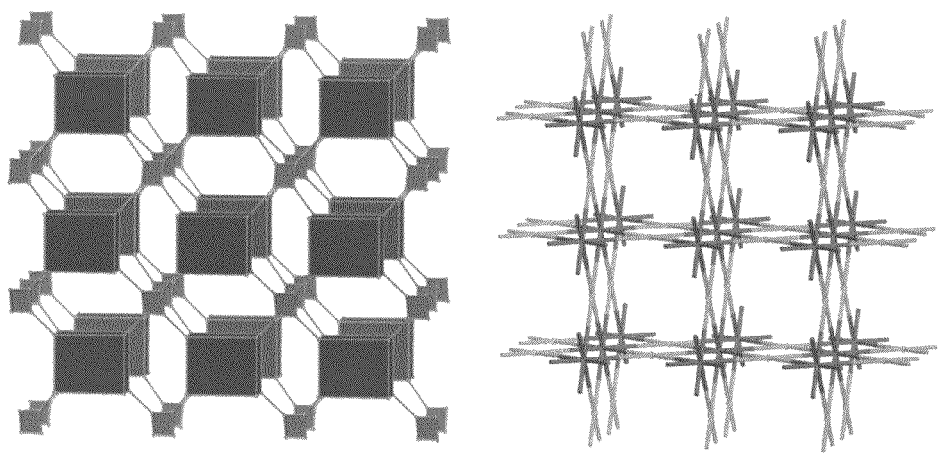

FIG. 9A shows the 8 coordinated distorted cubic SBU $Cu_4(OH)_2(CO_2)_8$. FIG. 9B shows the connection modes on the MOF having the ASV topology showing the 4 and 8 coordinated vertices.

Figure 10:
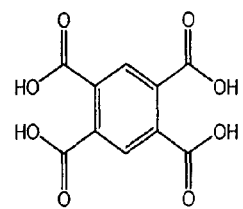
Figure 10:
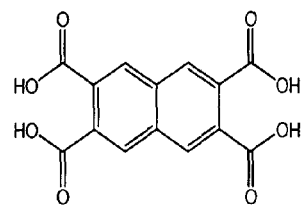
Figure 10:
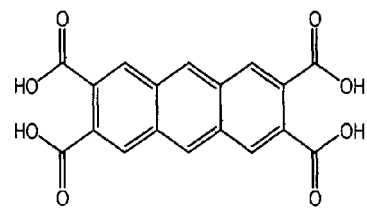

FIG. 10 shows 4-connected ligands suitable for assembly into zeolite like networks by their combination with the 8-coordinated SBUs, $Cu_4(OH)_2(CO_2)_8$.

Figure 11A:
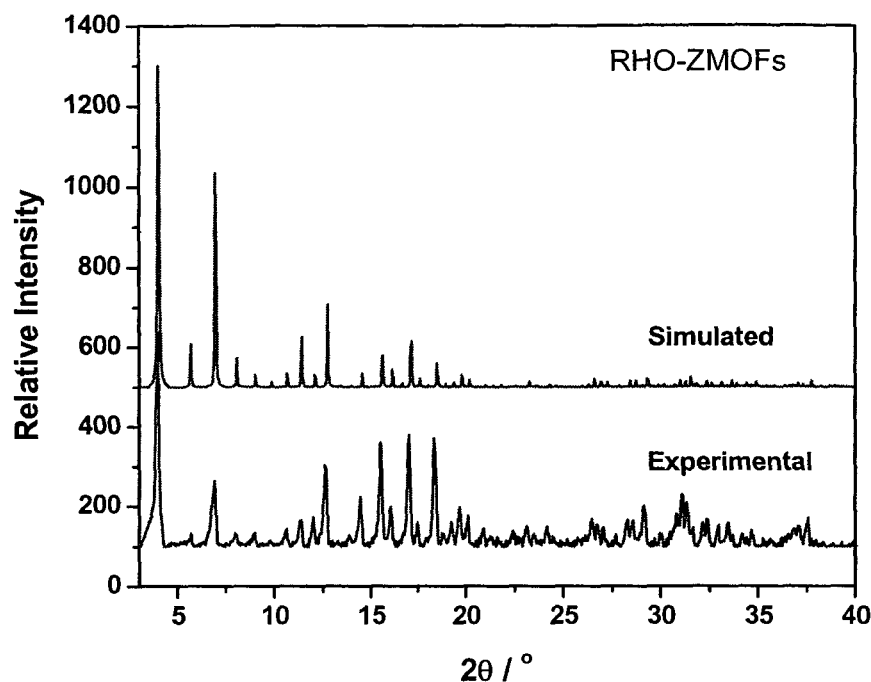
Figure 11B:
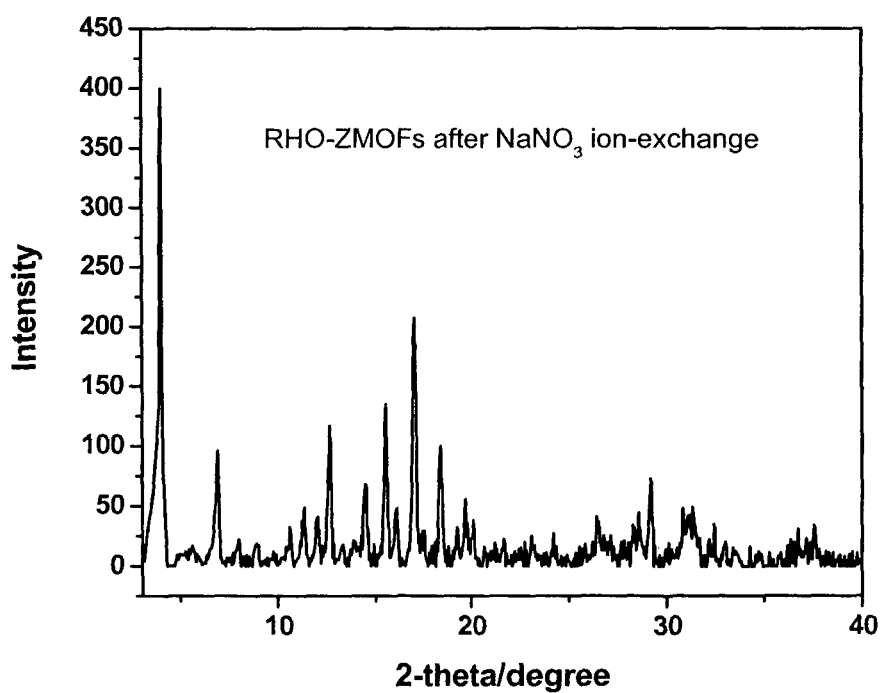
Figure 11C:
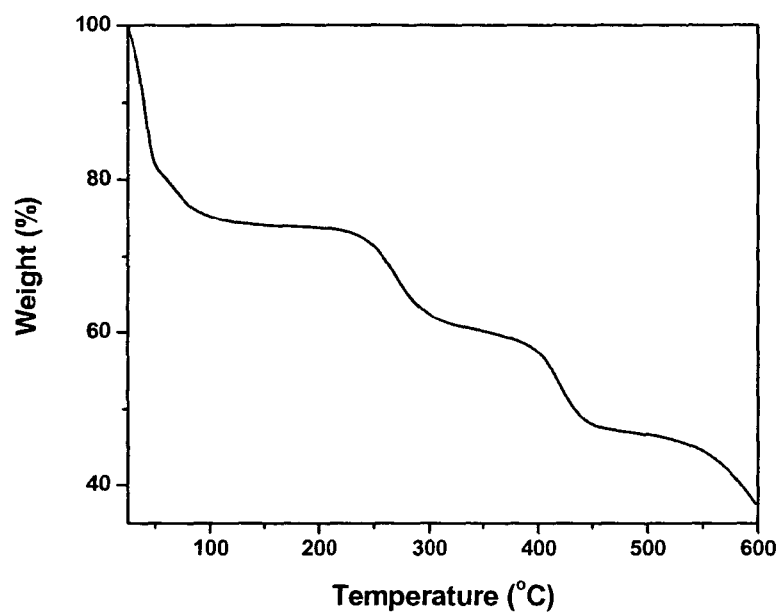

FIG. 11A shows experimental and simulated powder X-ray diffraction patterns for rho-ZMOFs prepared according to the methods of the subject invention. FIG. 11B shows powder X-ray diffraction pattern for Na ion exchanged rho-ZMOF prepared according to the methods of the subject invention. FIG. 11C shows the thermal gravimetric analysis (TGA) curve for the Na ion exchanged rho-ZMOF prepared according to the methods of the subject invention.

Figure 12A:
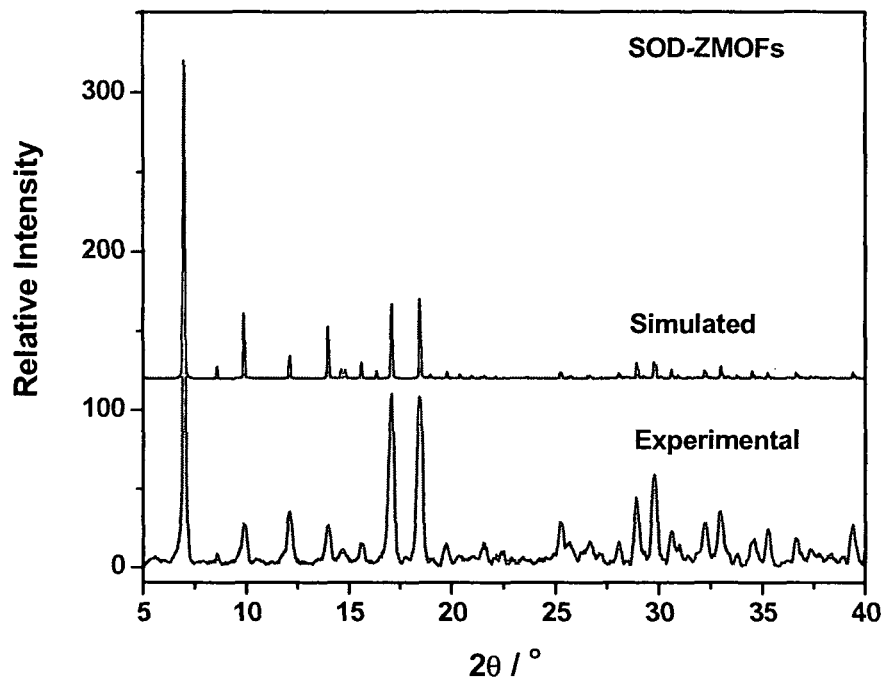
Figure 12B:
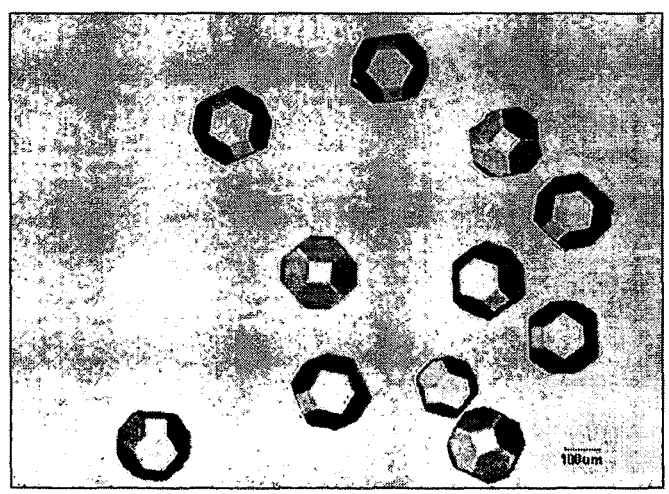

FIG. 12A shows experimental and simulated powder X-ray patterns for a specific embodiment of ZMOF with SOD topology. FIG. 12B shows a micrograph for a specific embodiment of ZMOF with SOD topology.

Figure 13A:
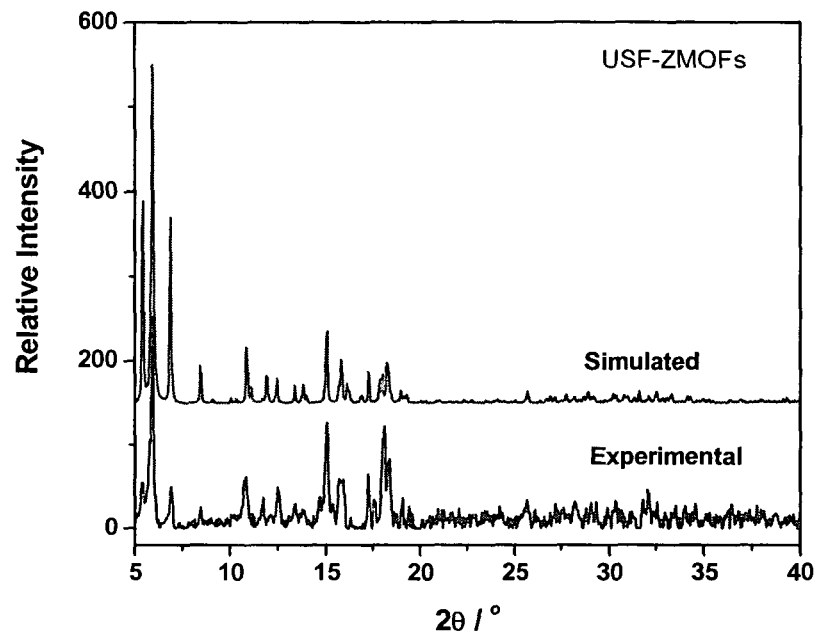
Figure 13B:
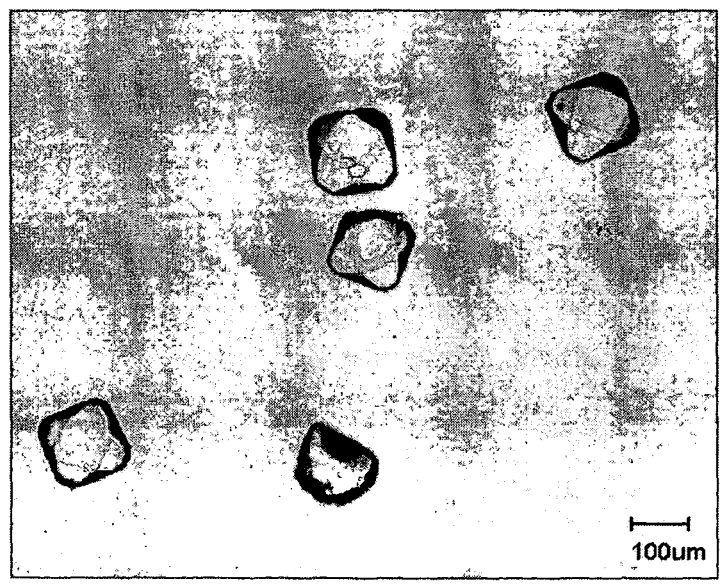

FIG. 13A shows experimental and simulated powder X-ray patterns for a specific embodiment of the USF-ZMOF. FIG. 13B shows a micrograph for a specific embodiment of the USF-ZMOF.

Figure 14:
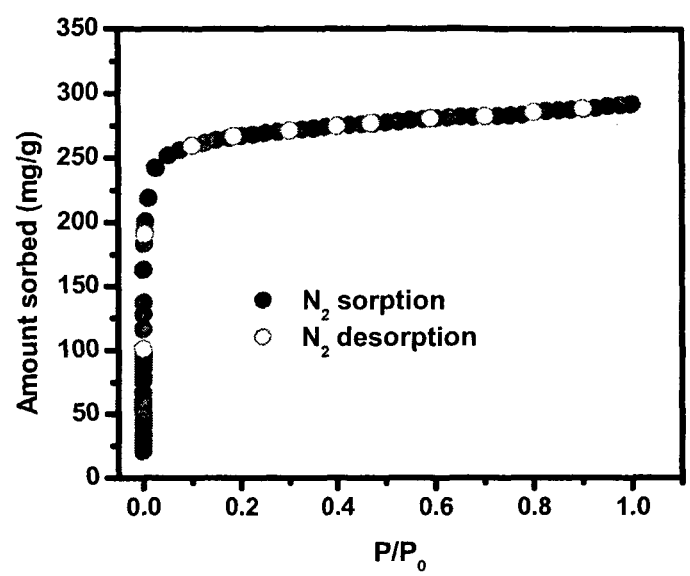

FIG. 14 shows Nitrogen gas sorption isotherm for RHO-ZMOFs at 78K.

Figures 15A, 15B:
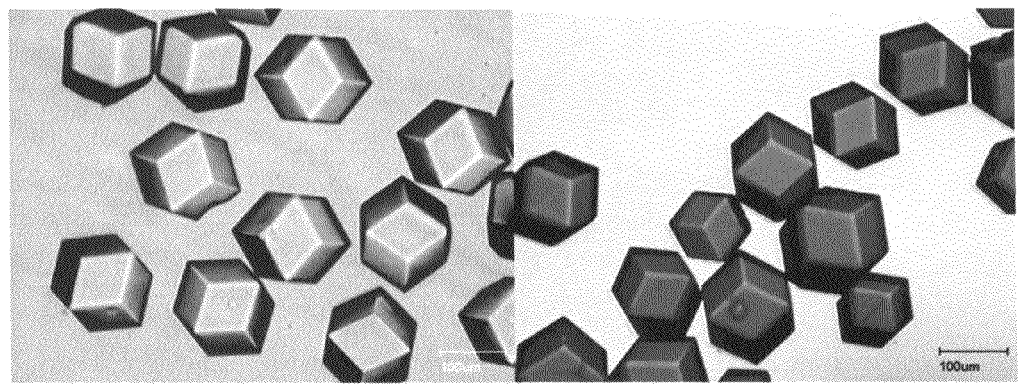
Figure 15C:
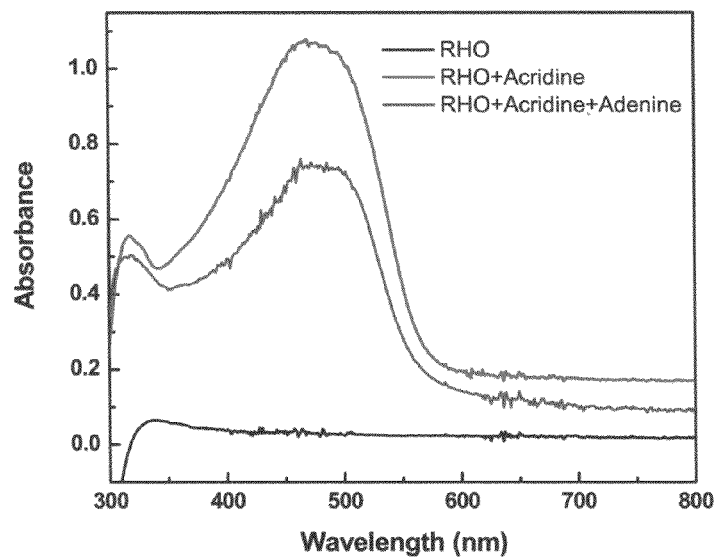

FIG. 15A shows a micrograph of rho-ZMOF prepared according to the methods of the subject invention. FIG. 15B shows a micrograph of rho-ZMOFs prepared according to the methods of the subject invention after acridine orange exchange. FIG. 15C shows the UV-vis spectra for the -rhoZMOF, rho-ZMOF with acridine orange.

Figure 16A:
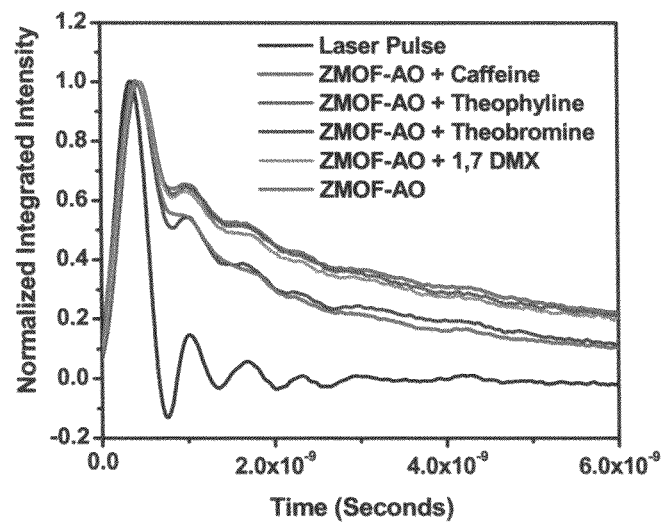
Figure 16B:
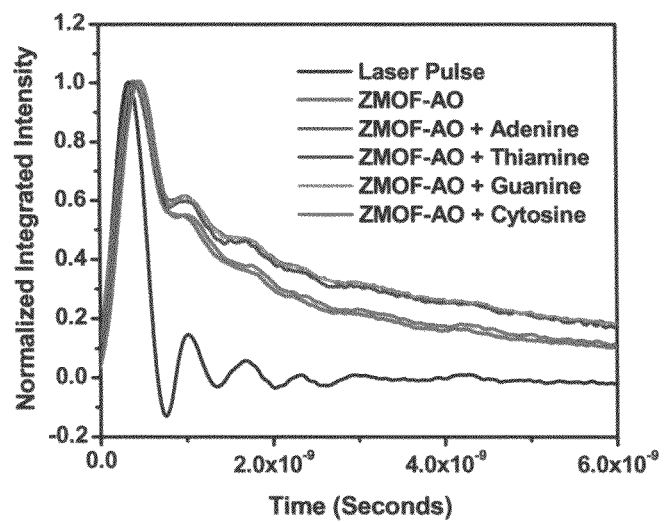

FIG. 16 shows fluorescence emission decays for a specific embodiment of ZMOF with AO in the presence of methyl xanthines and DNA nucleosides bases obtained with 355 nm excitation.

DETAILED DISCLOSURE OF THE INVENTION

The subject invention pertains to porous metal organic frameworks (MOFs) or assemblies having zeolite-net-like topologies, methods of their design and synthesis, and methods of using the framework. Specifically, the subject invention relates to the utilization of single metal ion based molecular building blocks (MBBs), via heterochelation and bridging, as a means toward the design and synthesis of metal-organic assemblies, both discrete and extended. This approach can utilize multifunctional ligands containing simultaneous chelating and bridging functionalities relative to the targeted metal ion. In one embodiment of the subject invention, an MBB is an $MX_nY_m$ cluster, wherein M is a metal ion; X is selected from the group consisting of N, O, and S; Y is selected from the group consisting of N, O, and S; n is at or within the range 2 to 4; and m is at or within the range 2 to 4.

Advantageously, the subject invention provides new strategies and pathways for the design and synthesis of rigid porous materials with large and tunable cavities from molecular building blocks. Specifically, porous materials having zeolite-net-like topologies and containing organic constituents in their framework are provided. A metal-ligand directed assembly approach is used to assemble rigid tetrahedral secondary building units and organic links with the commensurate geometry into expanded porous zeolite-net-like metal-organic frameworks (ZMOFs) with large cavities.

One of multiple complementary key steps suitable for the logical synthesis of crystalline metal-organic based assemblies is the ability to control the coordination number and thus geometry of inorganic and organic building units. The inorganic and organic building blocks can be judiciously predesigned to contain the required geometrical information and directional binding functionalities to facilitate the attainment of a predetermined structure. The approach of the present invention to the design and synthesis of robust metal-organic assemblies based on single metals as vertices is to render each heterocoordinated single metal, formed in situ, rigid and directional using nitrogen-oxygen chelates. The metal-nitrogen bonds will direct the topology, while the oxygen atoms will complete the coordination sphere of the metal and lock it into its position through the formation of rigid five-membered rings.

Construction of extended solids from molecular building blocks under mild conditions offers the ability to impart the desired functions and/or properties in the as-synthesized compound.

The disclosed new class of crystalline porous organic-containing materials is unique due to their related topologies to zeolites and can be regarded as a subclass of metal-organic frameworks.

The preparation of crystalline zeolite-like solids from molecular building blocks is correlated with controlling the geometry and the relative orientation of the molecular components in order that the resulting structures possess the desired zeolite topology, porosity, stability and physical properties. A new concept to construct rigid and directional secondary building units based on single metals is introduced. The subject invention's design approach and synthesis of robust metal-organic assemblies based on single metals as vertices is to render each hetero-coordinated single metal, formed in situ, rigid and directional using nitrogen-oxygen chelates. The metal-nitrogen bonds direct the topology, while the oxygen atoms (from the carboxylate) complete the coordination sphere of the metal and lock it into its position through the formation of rigid five membered rings. Other atoms capable of chelating the metal ion can also be used in the subject invention. This strategy has permitted the successful assembly of rigid tetrahedral secondary building units, $MN_4$, derived from the molecular building block ($MN_4(CO_2)_4$) and a suitable bent linker, under mild conditions, into zeolite-net-like metal-organic framework (ZMOFs). The disclosed porous ZMOFs are anionic and possess ion exchange capacity. The dual composition (periodic distribution the organic and inorganic components) of the disclosed materials and their extra-large cavities, two properties that are lacking in inorganic zeolites, offer great potential for their use in areas such as separation of large fine chemicals and hydrogen storage where inorganic zeolites are not suitable.

A specific embodiment of the subject invention is directed to zeolite-type metal organic frameworks (ZMOF). ZMOFs of the subject invention can have rho, sodalite, or the unprecedented topology USF-ZMOF (FIGS. 2A-2F), as well as other topologies known to the skilled artisan.

The use of single-metal-ion-based building units as means to synthesize other MOFs and discrete metal organic polyhedra is exemplified by the design and synthesis of the metal-organic cube MOC-1, the octahedron $M_6L_{12}$, the Kagomé lattice, and the newly designated USF-ZMOF.

In one embodiment, MBBs useful for the subject invention comprise those having the formula of a metal cluster $MN_xO_y$ (where x and y range from 1 to 4). In a specific embodiment, x=2 and y=2. In yet another specific embodiment, x=2 and y=3. In yet another specific embodiment, x=2 and y=4. In yet another specific embodiment, x=3 and y=2. In yet another specific embodiment, x=3 and y=3. In yet another specific embodiment, x=3 and y=4. In yet another specific embodiment, x=4 and y=2. In yet another specific embodiment, x=4 and y=3. In yet another specific embodiment, x=4 and y=4. The preferred embodiment comprises x=4 and y=4. The nitrogen and oxygen are provided by a suitable ligand.

M in the metal cluster is a metal cation of a metal selected from the group consisting of beryllium, zinc, cadmium, mercury, and any of the transition metals (in the periodic table scandium through copper, yttrium through silver, lanthanum through gold, and all known elements from actinium on). Preferably, M is zinc, copper, lanthanide, cadmium, nickel, iron, cobalt or indium.

The ligands have a potential to generate 5- or 6-membered rings when coordinated to the metal and, in addition, affords the bridging of two MBBs. The ligands are optionally rigid 5 or 6 member rings and their derivatives. Polytopic linkers containing both carboxylates and nitrogens as plausible coordinating groups are chosen. For ligands having both nitrogen and carboxylates, the carboxylate groups must be adjacent to nitrogen group α-position). The carboxylates lock the metals into their positions allowing the synthesis of rigid 8-coordinated, $MN_4O_4$, or 6-coordinated, $MN_4O_2$, cluster and thus a rigid framework. Examples of ligands include, but are not limited to, 1H-Imidazole-2-carboxylic acid, 1H-Imidazole-4-5-dicarboxylic acid, 2,7-Diaza-antracene-1,8-dicarboxylic acid, pyrimidine-4-6-dicarboxylic acid, pyridine-2,5,dicarboxylic acid, and 2,7-diaza-anthracene-3,6-dicarboxylic acid (FIG. 8).

It is to be understood that a ligand possessing multidentate groups may or may not bring with it one or more corresponding counter cations, such as $H^+$, $Li^+$, $Na^+$, $K^+$, $Mg^{2+}$, $Ca^{2+}$, $Sr^{2+}$, ammonium ion, alkylsubstituted ammonium ions, and arylsubstituted ammonium ions, or one or more counter anions, such as, $F^-$, $Cl^-$, $Br^-$, $I^-$, $ClO^-$, $ClO_2^-$, $ClO_3^-$, $ClO_4^{-,OH-}$, $HCO_2^-$, $NO_3^-$, $SO_4^{2-}$, $SO_3^{2-}$, $PO_4^{3-}$, $CO_3^{2-}$, and $PF_4^{3-}$ and organic counterions, for example, acetate $CH_3CO_2^{2-}$, and triphalates $CF_3SO_3^-$.

In one embodiment, the MBB comprises a metal ion having a coordination sphere and a ligand, wherein the ligand comprises chelation functionality and bridging functionality, and wherein the ligand chelation functionality completes the coordination sphere and directs the topology of the MBB and the resulting metal-organic frameworks. The bridging functionality serves to assemble the MBB with other MBBs to form a ZMOF.

Another specific embodiment is directed to ZMOFs having double four (4) member rings (FIGS. 9A and 9B). One example of a MBB used to assemble this type of ZMOF is $CU_4(OH)_2(CO_2)_8$.

Ligands useful in assembling double 4 member ring ZMOFs are those having four functional groups. Preferably, the functional group is a carboxylic acid having four connections. Ligands include, but are not limited to, benzene-1,2,4,5-tetracarboxylic acid, naphthalene-2,3,6,7-tetracarboxylic acid, and anthracene-2,3,6,7-tetracarboxylic acid (FIG. 10). Preferably, the ligand is benzene-1,2,4,5-tetracarboxylic acid.

ZMOFs of the subject invention include, for example and without limitation, the assembly of cube like building blocks $Cu_4(OH)_2(CO_2)_8$ with tetratopic linkers (FIG. 10)

Another aspect of the subject invention is directed to methods of synthesis of compounds of the subject invention. In a preferred embodiment, a method of synthesizing compounds of the subject invention comprises dissolving at least one metal salt and at least one ligand that has carboxylates adjacent to a nitrogen atom (i.e., elements having potential to make a coordination bond) in a solvent to form a solution, and crystallizing the solution. In one embodiment, the solvent is N,N-dimethyl formamide (DMF), ethanol, 4,4'-trimethylene-dipiperidine, or 1,2-diaminocyclohexane.

The metal salt is formed from a metal cation and an anion. The metal cation can be any metal in the periodic table. In one embodiment, the metal cation is selected from a group consisting of cations of beryllium, zinc, cadmium, mercury, and any of the transition metals (in the periodic table scandium through copper, yttrium through silver, lanthanum through gold, and all known elements from actinium on). The anion is selected from the group consisting of $F^-$, $Cl^-$, $Br^-$, $I^-$, $ClO^-$, $ClO_2^-$, $ClO_3^-$, $ClO_4^-$, $OH^-$, $HCO_2^-$, $NO_3^-$, $SO_4^{2-}$, $SO_3^{2-}$, $PO_4^{3-}$, $CO_3^{2-}$, and $PF_4^-$ and organic counterions, for example, acetate $CH_3CO_2^{2-}$, triphalates $CF_3SO_3^-$.

As noted above, the ligand possesses duel functionality—as a chelation agent of the metal and as a bridge to assemble other MBBs of the invention into metal organic frameworks. The ligand is optionally a rigid 5 or 6 member ring and its derivatives having both nitrogen and carboxylic acid groups. The carboxylic acid groups are adjacent to the nitrogen, and the nitrogen is a member of the ring. Examples of ligands include, but are not limited to, 1H-Imidazole-2-carboxylic acid, 1H-Imidazole-4-5-dicarboxylic acid, 2,7-Diaza-antracene-1,8-dicarboxylic acid, pyrimidine-4-6-dicarboxylic acid, pyridine-2,5,dicarboxylic acid, and 2,7-diaza-anthracene-3,6-dicarboxylic acid (FIG. 8). The ligand must also have the desired chelating groups. The bond angle between the N chelator and the metal ion dictates the topology of the MBB while the carboxylate's contribution to the coordination sphere renders the MBB rigid.

Advantageously, the synthesis of ZMOFs having topologies other than rho, including for example, but not limited to, sodalite (SOD) and the new topology seen in USF-ZMOF takes place according to the steps of the subject invention; however, changing the angle between nitrogen groups and/or using different structure directing agents is expected to permit the synthesis of other zeolite-net-like metal-organic frameworks having known zeolite topologies or completely unseen topologies in the inorganic zeolites Advantageously, rho-ZMOF-1 network is based on the assembly of the $MN_4O_4$ building block. These anionic networks should address the influence of the different cations on the sorption of hydrogen in porous metal-organic frameworks. ZMOF-1 (FIG. 1) is the first anionic metal-organic framework to be proven porous. Advantageously, various ZMOFs can be synthesized by assembling different ligands with the $MN_4O_4$ building blocks into novel ZMOFs or by using different structure directing agents as exemplified in both sod-ZMOF and usf-ZMOF.

Similarly metal-organic assemblies both discrete and extended can be constructed from rigid-directional building units $MN_xO_y$ (where x=2 to 4 and y=2 to 4) For example: the 3-connected MBBs like $MN_3O_3$ can be assembled into discrete cube (FIG. 4); the 4-connected MBBs like $MN_2O_4$ can be assembled into discrete octahedron (FIG. 5A-5D); the 4-connected MBBs like $MN_2O_4$ can be assembled into extended networks having Kagomé lattice (FIG. 6A-6D).

Advantageously, more than 100 different topologies (in addition to that of cubic diamond) are possible for linking tetrahedral building blocks together into structures with just one kind of vertex (O'Keeffe, M. et al., 1992). Accordingly, non-default structures can be targeted by judicious choice of the appropriately shaped SBUs and linkers. In order to synthesize a MOF with a zeolite-like topology, the T-X-T angle has to be close to the Si—O—Si angle of 145°, as observed in the case of inorganic zeolites (O'Keeffe, M. and Hyde, B. G., 1996). In addition, ZMOFs synthesized in accordance with the subject methods have rigid frameworks to withstand the evacuation of any molecules stored within the ZMOFs, even under vacuum evacuation.

Another preferred embodiment provides for reactions between indium salt and the imidazole dicarboxylic acid under predetermined reaction conditions (temperature, Ph, solvent, concentrations and amines acting as directing agents and conter-ions to balance the charge), which permit the construction of an extended 3-I network. Analysis of the structure revealed an as-synthesized 3-I network having a zeolite-like topology (Rho), which avoids the cubic diamond-like topology, as shown in FIGS. 1A-1F. In this structure, indium is coordinated to four nitrogen and four oxygen atoms to form an $MN_4O_4$ (FIG. 7) cluster having a dodecahedron geometry. The coordinated nitrogen atoms are directing the overall topology of the network and the oxygens are locking the metal into its position by forming four stable 5-member rings.

Figure 1A:
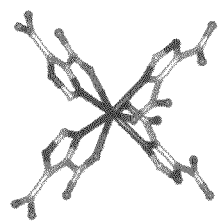
FIGS. 1A-1F show a single-crystal structure of rho-ZMOF.
Figure 1B:
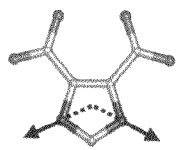
Figure 1C:
Figure 1D:
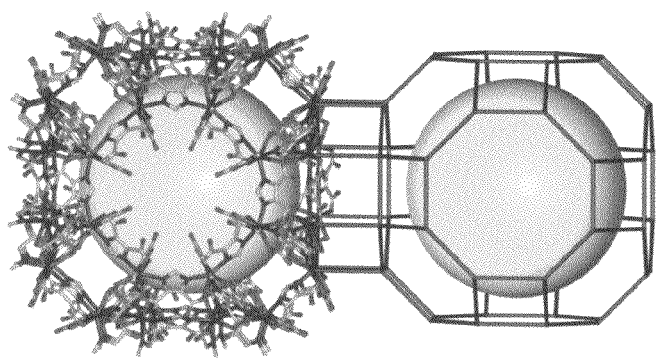
Figure 1E:
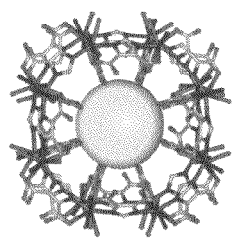
Figure 1F:
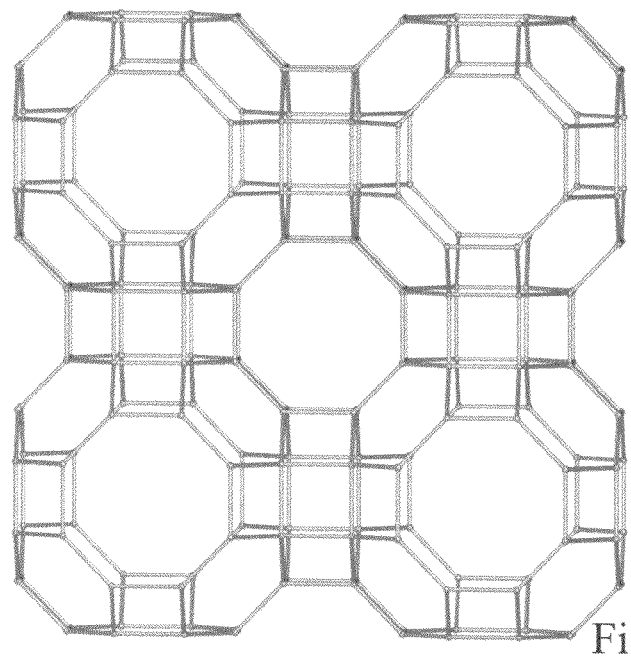
Figure 2A:
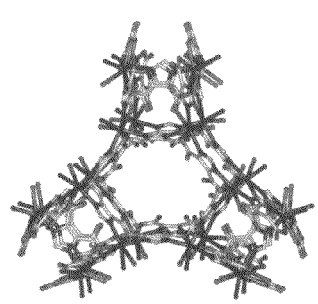
FIGS. 2A-F shows single-crystal structures of USF-ZMOF.
Figure 2B:
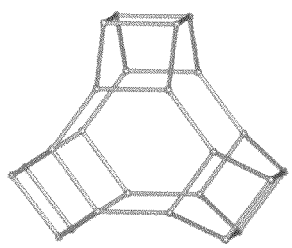
Figure 2C:
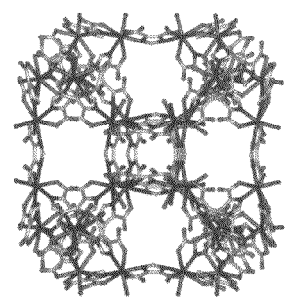
Figure 2D:
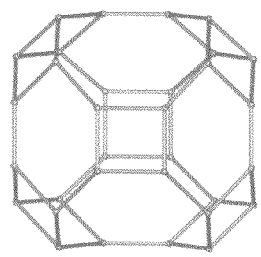
Figure 2E:
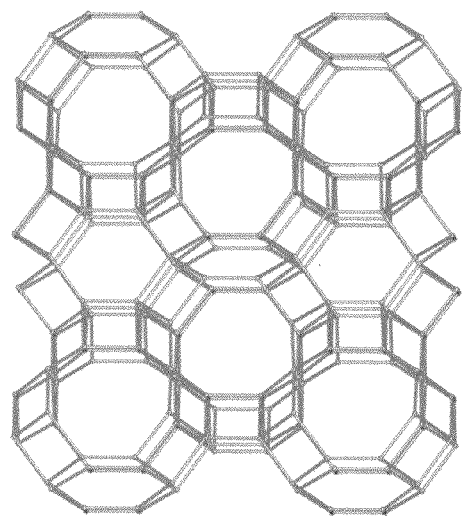
Figure 2F:
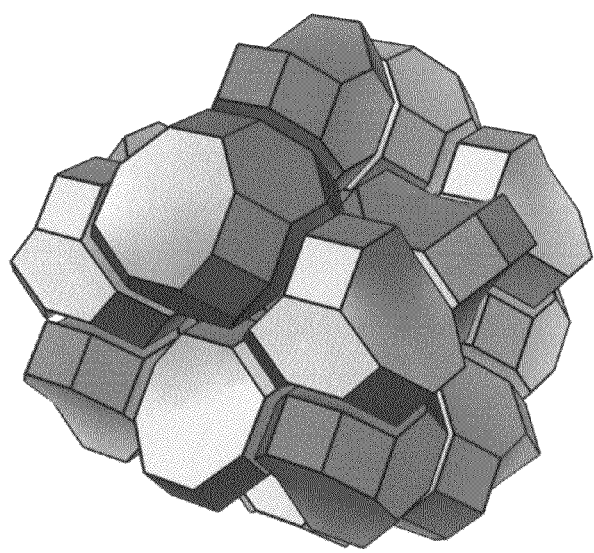

The as-synthesized structure is the first compound to contain an organic component and have a rho-like topology. The structure contains 4-, 6-, and 8-member rings fused together to form α-cages (FIG. 1A-1F) linked via a double 8-member ring (I8R) to form a decorated and extended rho-zeolite-like structure. The structure unit cell contains 48 indium atoms and 96 ligands to give an overall framework formula of ([$In_{48}$(ImHDC)$_{96}$]$^{48-}$)$_n$; the negatively charged framework is neutralized by 48 positive charges provided by either the singly or doubly charged ammonium derivatives used during the synthesis. The cavity volume of the structure shown in FIG. 1D is 8 times bigger than the silica based rho zeolite since the internal cavity diameter is doubled (2.96 nm vs 1.4 nm). Advantageously, the rho-ZMOF is insoluble in water and common organic solvents such as alcohols, DMF, benzene and acetone.

Thermogravimetrical analysis (TGA) and powder X-ray diffraction on the ZMOFs shown in FIGS. 11A-11C shows that the framework is stable to temperatures near 260° C. Advantageously, organic cations balancing the charge can be exchanged with several inorganic cations such as $Na^+$ and $Mg^{2+}$ without destructing the framework. The exchange is completed at room temperature and confirmed by elemental analysis; the structural integrity of the framework upon completion of the exchange is confirmed by the similarity between the X-ray powder diffraction pattern (XRPD) of the as-synthesized compound and the exchanged one. FIGS. 11A-11B, 12A, and 13A provide the X-ray patterns and micrographs of various embodiments of the subject ZMOFs including those exhibiting rho, SOD, and or USF topologies.

Preliminary studies in the case of Na-MOF-rho showed that the 240 water molecules residing in each of the α-cages of the exchanged structure could be completely removed at temperatures below 100° C. as confirmed by TGA and elemental analysis. The fully evacuated Na-MOF-rho derivative maintains its structural integrity as proven by X-ray powder diffraction analysis (FIG. 11B). Preliminary sorption data proves that the evacuated as-synthesized material, MOF-rho, and its exchange derivatives Na-MOF-rho and Mg-MOF-rho are all indeed porous; their nitrogen sorption isotherms are of type I isotherm and fully reversible characteristic of microporous materials with homogeneous pores. (FIG. 14).

Advantageously, changing the angle between the nitrogen groups provides optional methods to produce various zeolite topologies. The MOF-rho network is also the first framework based on the assembly of this new type of SBUs $MN_4O_4$ (FIG. 7).

Advantageously, the methods of the subject invention can be applied to 3-connected SBUs, for example $MN_3O_3$ FIGS. 4A and 4B and 4-connected $MN_2O_4$ (FIG. 5 and FIG. 6) for assembly into extended networks or discrete assemblies.

The subject invention also concerns methods for synthesizing a metal organic framework. In one embodiment the method comprises reacting a metal salt and a ligand having chelating and bridging functionality relative to the metal ion of said metal salt, in a suitable solvent, in the presence of a structure directing agent (SDA) and crystallizing the solution. Examples of SDAs include, but are not limited to, 1,3,4,6,7,8-hexahydro-2H-pyrimido[1,2-α]pyrimidine (HPP), imidazole, 4,4'-trimethylenedipiperidine, or 1,2-diaminocyclohexane. In one embodiment the crystallizing step comprises heating said solution from about room temperature to about 200° C. for at least about 4 to 12 hours. In a specific embodiment, the crystallizing step comprises heating at about 80° C. to about 90° C. for at least 10 hours followed by heating at about 95° C. to about 110° C. for at least 12 hours. In an exemplified embodiment, the SDA is HPP and the crystallizing step comprises heating at about 85° C. for about 12 hours followed by heating at about 100° C. for about 14 hours. In another exemplified embodiment, the SDA is imidazole and the crystallizing step comprises heating at about 85° C. for about 12 hours followed by heating at about 105° C. for about 23 hours. In one embodiment, a metal of the metal salt has a minimum coordination number of six and a maximum of eight. The metal of the metal salt can be any metal in the periodic table including, for example, beryllium, zinc, cadmium, mercury, or any of the transition metals (in the periodic table scandium through copper, yttrium through silver, lanthanum through gold, and all known elements from actinium on). In a specific embodiment, the metal of the metal salt is zinc, copper, lanthanide, cadmium, nickel, iron, cobalt or indium. In an exemplified embodiment, the metal salt is $M(NO_3)_3$. In one embodiment, the ligand can be any of 1H-Imidazole-2-carboxylic acid, 1H-pyrrole-2,4-dicarboxylic acid, 1H-Imidazole-4-5-dicarboxylic acid, 2,7-Diaza-antracene-1,8-dicarboxylic acid, pyrimidine-4-6-dicarboxylic acid, pyridine-2,5,dicarboxylic acid, or 2,7-diaza-anthracene-3,6-dicarboxylic acid. In one embodiment, a solvent used in the subject method can be any of N,N-dimethyl formamide (DMF), acetonitrile, and/or ethanol.

Another specific embodiment of the subject method is directed to zeolite frameworks based on double four member ring by assembling a presynthesized in situ double 4-member ring SBUs (cube-like) with a four-connected organic building blocks. Synthetic pathways and experimental conditions were found to synthesize in situ two eight coordinated secondary building units namely the neutral $Cu_4(OH)_2(CO_2)_8$. The MBBs have cube-like topology (FIG. 9A). Linkers useful in the method of synthesizing a network of double 4-member rings comprise ligands having four-connection building blocks. Examples include, but are not limited to, 1,2,4,5-benzene tetracarboxylate, naphthalene-2,3,6,7-tetra-carboxylic acid, and anthracene-2,3,6,7-tetracarboxylic acid (FIG. 10).

Preliminary attempts to assemble copper ions with a tetra-carboxylate linker, 1,2,4,5-benzene tetracarboxylate, have permitted the construction of two novel networks having a zeolite topology. The crystalline compound was analyzed by single X-ray diffraction. The structure has the same topology as the zeolite ASV, and their connectivity resembles the ASV. Advantageously, compounds produced according to the subject method offer the possibility to tune the pore dimension and functionality by utilizing expanded linkers based on aromatic benzene rings and thus possibility the increase the hydrogen uptake due to the augmentation of sorption sites on the network (FIG. 9B).

Another aspect of the subject invention is directed to a design strategy for synthesizing other highly porous ZMOFs. The design strategy comprises providing a targeted network; deconstructing the targeted network into its basic building blocks, enumerating a plurality of plausible structures based on the assembly of preselected molecular building blocks, selecting a metal that permit when coordinated to chelation functional groups the desired MBB, and provide a polytopic ligand capable of providing the desired topological angle and capable of saturating the metal and locking the metal in a rigid position with chelation functional groups. Advantageously, the MBBs of the subject invention provide a variety of useful MBBs for use in this design strategy. However, any MBB having the required metal, angles, and geometries can be used. Numerous ligands as disclosed in this application are also available to design the appropriate ZMOF.

Yet another aspect of the subject invention is directed to methods of storing materials in ZMOFs of the subject invention. Advantageously, gases, drugs, sensors, entities possessing charge and large molecule, as well as other materials, can be stored within the ZMOFs. These ZMOFs can also be used as catalysts or enzymes in various chemical and biochemical reactions. Additionally, the ZMOFs of the subject invention are useful as sensing devices when preselected probes are encapsulated within their cavities.

As used in this specification and the appended claims, the singular forms "a", an and "the" include plural reference unless the context clearly dictates otherwise. Thus, for example, a reference to "a ZMOF" includes more than one such ZMOF, a reference to "a metal-organic assembly" includes more than one such assembly, a reference to "a ligand" includes more than one such ligand, and the like.

The term "heterochelation" or "heterocoordination" refers to a metal ion whose coordination sphere is completed by ligands that exhibit chelation by at least two different atoms within the surrounding ligand moieties. For example, 4,5-H2-ImDC, can heterochelate the metal by using two different donor groups namely an oxygen atom from the carboxylate and a nitrogen atom from the imidazole ring. Heterochelation refers to the functional groups directly coordinated to the metal and different and belong to the same generated ring. In the case of $MN_4(CO2)_4$, the metal is chelated by 4 (O—, N—) pairs to form 4 five membered rings around the metal. Additionally, the heterochelating groups are not limited to nitrogen and oxygen but can be expanded to a combination of any two from the following nitrogen, oxygen, sulfur and any other element capable of chelating the selected metal ion.

All patents, patent applications, provisional applications, and publications referred to or cited herein are incorporated by reference in their entirety, including all figures and tables, to the extent they are not inconsistent with the explicit teachings of this specification.

Materials and Methods

Synthesis of rho-ZMOF:

4,5-Imidazoledicarboxylic acid (0.014 g, 0.087 mmol), $In(NO_3)_3.2H_2O$ (0.015 g, 0.0435 mmol), DMF (1 mL), $CH_3CN$ (1 mL), 1,3,4,6,7,8-hexahyrdro-2H-pyrimido[1,2-α] pyrimidine (HPP) (0.2 mL, 0.42 M in DMF), and $HNO_3$ (0.125 mL, 3.5 M in DMF) were added respectively to a 20-mL vial, which was sealed and heated to 85° C. for 12 h and 100 °C. for 14 h, then cooled to room temperature. The colorless polyhedral crystals were collected and air-dried, yielding 0.0175 g (64% based on $In(NO_3)_3.2H_2O$). CHN elemental analysis (%) for rho-ZMOF, $In_{48}(C_5N_2O_4H_2)_{96}(C_7N_3H_{15})_{24}(DMF)_{36}(H_2O)_{192}$ Calcd. C, 30.49; H, 4.02; N, 14.11. Found C, 29.82; H, 4.08; N, 14.06. FT-IR (4000-600 $cm^{-1}$): 3416(br), 1657(w), 1571(m), 1474(s), 1400(m), 1323 (w), 1302(w), 1252(m), 1108(s), 1015(w), 980(w), 836(m), 781(s).

$Na^+$-exchanged rho-ZMOF: $In_{48}(C_5N_2O_4H_2)_{96}Na_{48}(C_2H_5OH)_{96}(H_2O)_{192}$ Calcd. C, 27.56; H, 3.96; N, 9.18. Found C, 27.36; H, 3.65; N, 9.14.

Atomic absorption result: Calcd, Na, 3.77%. Found Na, 3.9%.

Synthesis of sod-ZMOF:

4,5-Imidazoledicarboxylic acid (0.021 g, 0.1305 mmol), $In(NO_3)_3.2H_2O$ (0.015 g, 0.0435 mmol), DMF (1.5 mL), $CH_3CN$ (0.5 mL), Imidazole (0.2 mL, 1.5 M in DMF), and $HNO_3$ (0.3 mL, 3.5 M in DMF) were added respectively to a 20-mL vial, which was sealed and heated to 85° C. for 12 h and 105° C. for 23 h. The colorless polyhedral crystals were collected and air-dried yielding 0.021 g (54% based on $In(NO_3)_3.2H_2O$). CHN elemental analysis (%) for sod-ZMOF, $In_4(C_5N_2O_4H_2)_2(C_3N_2H_5)(DMF)_4(CH3_2CN)(H_2O)_4$ Calcd. C, 36.13; H, 5.39; N, 17.17. Found C, 37.07; H, 4.92; N, 17.18.

Synthesis of USF-ZMOF 4,5-Imidazoledicarboxylic acid (0.014 g, 0.087 mmol), $In(NO_3)_3.2H_2O$ (0.015 g, 0.0435 mmol), DMF (1 mL), $CH_3CN$ (1 mL), $H_2O$ (0.5 mL), 1,2-diaminocyclohexane (0.1 mL, 1.75M in DMF), and $HNO_3$ (0.5 mL, 0.35 M in DMF) were added respectively to a 20-mL vial, which was sealed and heated to 85° C. for 12 h. The colorless polyhedral crystals were collected and air-dried, yielding 0.023 g (56% based on $In(NO_3)_3.2H_2O$). Elemental microanalysis for USF-ZMOF, $In_{2.5}(C_5N_2O_4H_2)_5(C_6N_2H_{16})_{1.25}(DMF)_{12}(CH3CN)_3(H_2O)_8$ Calcd. C, 38.12; H, 5.97; N, 16.41. Found C, 38.34; H, 6.23; N, 16.19. FT-IR spectrum of as-synthesized USF-ZMOFs: ($cm^{-1}$) 1655(s), 1579(m), 1465(s), 1439(w), 1388(s), 1329(w), 1311(w), 1252(m), 1107(s), 1060(w), 1024(w), 848(m), 783(s), 656(vs). These ZMOFs compounds were insoluble in water and all common organic solvents such as ethanol, acetone, acetonitrile, benzene, tetrahydrofuran, N,N'-dimethylformamide, N,N'-diethylformamide, and dimethyl sulfoxide.

Synthesis of $[Ni_8(HImDC)_{12}]^{8-}$:

4,5-Imidazoledicarboxylic acid (0.065 mmol), $Ni(NO_3)_2.6H_2O$ (0.044 mmol), DMF (1 mL), EtOH (1 mL), 4,4'-trimethylenedipiperidine (0.1 mL, 0.95 M in DMF), and $HNO_3$ (0.2 mL, 0.35 M in DMF) added to a 20 mL vial. Solution heated at 85° C. for 12 h, then cooled to room temperature. Blue color cubic crystals collected and air-dried (82%) yield). The as-synthesized material is insoluble in water and common organic solvents. CHN elemental analysis (%) for $[Ni_8(HImDC)_{12}]^{-8}$, $C_{132}H_{200}N_{36}O_{62}Ni_8$: calcd. C, 42.24; H, 5.37; N, 13.44; found C, 42.11; H, 5.23; N, 13.43, FT-IR (4000-600 $cm^{-1}$): 1655 (m), 1560 (w), 1477 (vs), 1410 (m), 1302 (m), 1252 (m), 1110 (m), 843 (m), 783 (m), 661 (vs). Crystal data for $[Ni_8(HImDC)_{12}]^{-8}$: $C_{132}H_{200}N_{36}O_{62}Ni_8$: $M_r$=3752.96, monoclinic, $P2_1/c$, a=16.086(2), b=28.306(3), c=21.617(2) Å, β=102.189(2)°, V=9621(2) $Å^3$, Z=2, $D_c$=1.295 g $cm^3$, µ=0.85 $mm^{-1}$, 19870 [R(int)=0.0733] unique reflections of which 11 110 assumed as observed (I>2σ(I)). Final R1=0.0961, wR2=0.2793 (I>2σ (I)). CCDC 243500. See http://www.rsc.org/suppdata/cc/b4/b409459j/ for crystallographic data in .cif or other electronic format.

Preparation of In(2,5-PDC)$_2$(HTMDP)(EtOH)(H$_2$O)$_2$ 2,5-H$_2$PDC (14.5 mg, 0.087 mmol), In(NO$_3$)$_3$.2H$_2$O (15.0 mg, 0.044 mmol), EtOH (1 mL), H$_2$O (1 mL), TMDP (0.1 mL, 0.95 M in DMF), and HNO$_3$ (0.2 mL, 0.35 M in H$_2$O) were added to a vial, and the solution was heated to 85° C. for 12 h. Colorless polyhedral crystals were collected and air-dried (17.6 mg, 62% yield). As-synthesized material is insoluble in H$_2$O and common organic solvents. Elemental analysis (%) for In(2,5-PDC)$_2$(HTMDP)(EtOH)(H$_2$O)$_2$, C$_{27}$H$_{33}$N$_4$O$_8$In calcd: C, 49.36; H, 5.03; N, 8.53; found: C, 48.67; H, 4.93; N, 8.71.

Preparation of In$_6$(2,5-PDC)$_{12}$(1,2-H$_2$DACH)$_2$(DMF)$_5$(EtOH)$_5$H$_3$O)$_2$ 2,5-H$_2$PDC (14,5 mg, 0.087 mmol), In(NO$_3$)$_3$.2H$_2$O (15.0 mg, 0.044 mmol) EtOH (1 mL), DMF (2 mL), 1,2-diaminocyclohexane (1,2-DACH) (0.1 mL, 0.4 M in DMF), and HNO$_3$ (0.25 mL, 0.35 M in DMF) were added to a vial, and the solution was heated to 85° C. for 12 h. Colorless rodlike crystals were collected and air-dried (18.6 mg, 73% yield). As-synthesized material is insoluble in H$_2$O and common organic solvents. Elemental analysis (%) for In$_6$(2,5-PDC)$_{12}$(1,2-H$_2$DACH)$_2$(DMF)$_5$(EtOH)$_5$(H$_3$O)$_2$, C$_{121}$H$_{139}$N$_{21}$O$_{60}$In$_6$ calcd: C, 41.06; H, 3.96; N, 8.32; found: C, 41.89; H, 3.67; N, 8.54. In(2,5-PDC)$_2$(HTMDP)(EtOH)(H$_2$O)$_2$ can also be synthesized using conditions similar to those for In$_6$(2,5-PDC)$_{12}$(1,2-H$_2$DACH)$_2$(DMF)$_5$(EtOH)$_5$(H$_3$O)$_2$ with the only difference being the choice of the template.

Crystallographic Data of In$_6$(2,5-PDC)$_{12}$(1,2-H$_2$DACH)$_2$(DMF)$_5$(EtOH)$_5$(H$_3$O)$_2$:

C$_{121}$H$_{139}$In$_6$N$_{21}$O$_{60}$, M=3536.45, triclinic, space group P1, a=14.4111(13) Å, b=16.0466(14) Å c=16.7388-(15) Å, α=114.216(2)°, β=95.441(2)°, γ=91.595(2)°, V=3504.8-(5) Å$^3$, Z=1. Final R indicates (I>2σ(I)): R$_1$=0.0855, wR$_2$=0.2155.

Crystallographic Data of In(2,5-PDC)$_2$(HTMDP)(EtOH)(H$_2$O)$_2$:

C$_{27}$H$_{33}$InN$_4$O$_8$, M=656.39, trigonal space group R3c, a=b=15.7870(19) Å, c=51.509(13) Å, V=11118(3) Å$^3$, Z=18. Final R indicates (I>2σ(I)): R$_1$=0.0651, wR$_2$=0.1192.

Crystal Data for rho-ZMOF.

C$_{10}$H$_4$InN$_4$O$_4$: Cubic, Im-3m, a=31.0622(7) Å, V=29970.7(12) Å$^3$, Z=48, Final R=0.0590, wR2=0.1512 (for 878 unique reflections assumed as observed with I>2σ(I)).

Crystal data for sod-ZMOF.

C$_{10}$H$_4$InN$_4$O$_8$: Cubic, Fd-3c, a=36.0435(11) Å, V=46825(2) Å$^3$, Z=96, Final R=0.0872, wR2=0.2334 (for 1174 unique reflections assumed as observed with I>2σ(I)).

EXAMPLE 1

N$_2$ Sorption on rho-ZMOF-1 @78 K (FIG. 14)

Increments of nitrogen gas were introduced into a chamber containing the framework of rho-MOZ-1 of the subject invention. The temperature was held constant at 78 K. The resulting weight changes were recorded and plotted. The plateau was reached relatively quickly.

By applying the Langmuir and DR equations, the Langmuir surface area and pore volume, respectively, were estimated to be S$_L$=843 m$^2$/g and V$_p$=0.32 cm$^3$/g.

EXAMPLE 2

Zeolite Metal-Organic Framework (rho-ZMOF) Containing Acridine Orange

Acridine orange (AO) was encapsulated within a rho-ZMOF of the subject invention (FIG. 14A). Analysis of the UV-visible spectra of acridine orange encapsulated metal organic framework zeolites shows that the AO is encapsulated in the cavities of ZMOF two components with lifetimes ~2 ns and ~11 ns (FIG. 14B). Analysis of the fluorescence lifetimes of metal organic zeolites containing acridine orange incubated with methyl xanthines or DNA nucleosides bases show an increase in amplitude of the fast component but no effect on the long lifetime component (FIG. 15).

EXAMPLE 3

Preparation of Indium MBB

Reaction between 2,5-H$_2$PDC and In(NO$_3$)$_3$.2H$_2$O in an EtOH/H$_2$O solution in the presence of 4,4'-trimethylenedipiperidine (TMDP) yields a homogeneous microcrystalline material. The as synthesized compound was characterized and formulated by elemental microanalysis and single-crystal X-ray diffraction studies as In(2,5-PDC)$_2$(HTMDP)(EtOH)(H$_2$O)$_2$ (1). The purity of 1 was confirmed by similarities between simulated and experimental X-ray powder diffraction (XRPD). In the crystal structure of 1 (FIG. 6A-6D), each indium metal ion is coordinated to two nitrogen atoms and four oxygen atoms of four independent 2,5-PDC ligands, respectively, to form an octahedral surrounding In(III) in the MBB, InN$_2$(CO$_2$)$_4$. Each independent 2,5-PDC is coordinated to two In(III) metals by forming a five-membered ring via N— and O— heterochelation, and in a monodentate fashion through the carboxylate in the 5-position. InN$_2$(CO$_2$)$_4$ where the In—N bonds and In-(5-carboxylate) bonds direct the topology (positioning each In at 120° vis-à-vis 2,5-PDC) and the α-carboxylate oxygens merely complete the In(III) coordination sphere, can be regarded as a quasi-planar 4-connected building unit, cis-InN$_2$—(CO$_2$)$_2$ (FIG. 6B). The assembly of the 4-connected nodes results in the generation of three- and six-membered windows to give an overall Kagomé lattice topology. To our knowledge, metal-organic frameworks with Kagomé lattice topology are scarce, even though inorganic Kagomé compounds are relatively abundant.

A trans pyramidal InN$_2$(CO$_2$)$_2$ building unit has been produced from the reaction of the same starting materials in N,N'-dimenthylfomamide (DMF), EtOH, and 1,2-diaminocyclohexane (1,2-DACH), which gives rodlike crystals formulated as In$_6$(2,5-PDC)$_{12}$(1,2-H$_2$DACH)$_2$(DMF)$_5$(EtOH)$_5$(H$_3$O)$_2$ (2) by elemental microanalysis and single-crystal X-ray diffraction studies. The crystallographic analysis of 2 revealed that its structure is composed of discrete metal-organic octahedral, [In$_6$(2,5-PDC)$_{12}$]. In the crystal structure of 2 (FIG. 5A-5F), each anionic octahedron resides in position around the crystallographic center of symmetry and consists of six In(III) ions occupying the vertexes of the octahedron linked by 12 2,5-PDC ligands, forming the octahedron edges. Each In(III) ion is coordinated to two nitrogen and five oxygen atoms (InN$_2$(CO$_2$)$_4$) from four 2,5-PDC ligands (FIG. 5B). As in 1, the In—N bonds and the In-(5 carboxylate) bonds direct the topology while the α-carboxylates complete the metal ion coordination sphere, resulting in a 4-connected node, InN$_2$(CO$_2$)$_2$. Distortion from the ideal octahedron can be characterized by the maximal deviation from the average In—In distance value (8.378 Å) and from the In—In—In ideal angles of 60° and 90°; 0.192 Å (2.29%), 2.61° (4.35%), and 0.28° (0.31%), respectively (see Supporting Information). The isolated octahedron, $[In_6(2,5-PDC)_{12}]^{6-}$, possesses an overall $T_h$ symmetry.

Interesting structural features of compound 2 are its internal cavity and triangular windows. The cavity of the octahedron cluster encapsulates one EtOH molecule, which is statistically disordered around the center of symmetry. Six DMF and two EtOH molecules are partially situated in the eight triangular windows of the octahedron. The remaining EtOH and $H_2O$ molecules are located in the interstices between the octahedral. The discrete octahedra are linked by cis-1,2-$H_2DACH$ via N—H•••O hydrogen bonds to generate a 3-D network.

Although a mixture of isomers of 1,2-DACH can be used in the synthesis, only the cis isomer is found to direct the formation of 2. Therefore, cis-1,2-DACH acts as a structure directing agent and, as a result, compound 2 offers potential for separation and recognition of the cis and trans isomers of 1,2-DACH. It should also be noted that crystal structures containing the cis isomer are rare.

EXAMPLE 4

Directed Assembly of Metal-Organic Cubes from Deliberately Predesigned Molecular Building Blocks Octahedrally-coordinated nickel ions prefer facial geometry, in this case fac-$NiN_3O_3$, when chelated in a five-membered fashion by N— and O— of ligand. A bis(bidentate) ligand, such as 4,5-imidazoledicarboxylic acid ($H_3ImDC$), permits formation of such five-membered rings (coplanar with the imidazole ring), and thus coordination with nickel will lead to the construction of a metal-organic cube, where the metal-nitrogen bonds direct the topology. Indeed, reaction of $H_3ImDC$ and $Ni(NO_3)_2.6H_2O$ in N,N'-dimethylfomamide (DMF), ethanol (EtOH) and 4,4'-trimethylenedipiperidine (TMDP) gives blue cubic crystals containing the expected metal-organic cube, MOC-1, $[Ni_8(HImDC)_{12}]^{8-}$. The as-synthesized compound is formulated as $Ni_8(HImDC)_{12}$—$(H_2TMDP)_4(DMF)_4(EtOH)_4(H_2O)_6$ (3) by elemental microanalysis and single-crystal X-ray diffraction studies.

In the crystal structure of 3 (FIG. 4), each anionic cube $[Ni_8(HImDC)_{12}]^{8-}$ resides in position around the crystallographic center of symmetry and consists of eight $Ni^{2+}$ ions occupying the vertices of the cube, and linked in a bidentate fashion by twelve HImDC exo-ligands. Each Ni ion is coordinated to three nitrogen and three oxygen atoms from three separate HImDC ligands, producing the facial octahedral coordination geometry, fac-$MN_3O_3$. Each ligand, stabilized by the strong intramolecular O—H•••symmetrical hydrogen bond (O•••O in the range 2.50-2.55 Å), chelates two individual nickel ions to form two five-membered rings coplanar with the imidazole ring. The regularity of the cube is indicate by the fact that Ni—Ni—Ni angles lie between 88.28(1)° and 91.85(1)°, and the Ni—Ni distances along the edges are all in a narrow range 6.299-6.333 Å. The distance from the cube center to the closest non-hydrogen atom of the imidazole ring, C3, is 3.93 Å, thus the inner cavity has an estimated volume of ~50 Å$^3$. The isolated MOC-1 does not host any molecules in its cavity, and possesses an overall $T_h$ symmetry.

It should be understood that the examples and embodiments described herein are for illustrative purposes only and that various modifications or changes in light thereof will be suggested to persons skilled in the art and are to be included within the spirit and purview of this application.

REFERENCES

Caulder, D. L. and K. N. Raymond (1999) "Supermolecules by Design" *Acc. Chem. Res.*, 32:975.

Cheetham, A. K., G. Ferey and T. Loiseau (1999) *Angew. Chem., Int. Ed.*, 38:3268.

Chui, S. S.-Y., S. M.-F. Lo, J. P. H. Charmant, A. G. Orpen and I. D. Williams (1999) "A Chemically Functionalizable Nanoporous Material $[Cu_3(TMA)_2(H_2O)_3]_n$" *Science*, 283:1148.

Corma, A. and Davis, M. E. (2004) *Chem Phys Chem* 5:304.

Davis, M. E. (1997) *Chem-Eur. J.* 3:1745.

Davis, M. E. (1993) "New vistas in zeolite and molecular sieve catalysis" *Acc. Chem. Res.*, 26:111-115.

Davis, M. E. (2002) "Ordered porous materials for emerging applications" *Nature*, 417: 813-821.

Desiraju, G. R. (2001) "Chemistry Beyond the Molecule" *Nature*, 412:397.

Eddaoudi, M., D. B. Moler, H. Li, B. Chen, T. M. Reineke, M. O'Keeffe and O. M. Yaghi (2001) "Modular Chemistry: Secondary Building Units as a Basis for the Design of Highly Porous and Robust Metal-Organic Carboxylate Frameworks" *Acc. Chem. Res.*, 34:319.

Evans, O. R.; Lin, W. (2002) "Crystal Engineering in NLO Materials Based on Metal-Organic Coordination Networks" *Acc. Chem. Res.*, 35:511-522.

Hoskins, B. F. and R. Robson (1990) "Design and Construction of a New Class of Scaffolding-like Materials Comprising infinite Polymeric Frameworks of 3D-Linked Molecular Rods. A Reappraisal of the $Zn(CN)_2$ and $Cd(CN)_2$ Structures and the Synthesis and Structure of the Diamond-Related Frameworks $[N(CH_3)_4][Cu^IZn^{II}(CN)_4]$ and $Cu^I[4, 4'',4'',4'''$-tetracyaiiotetraphenylmethane]$BF_4.xC_6H_5NO_2$" *J. Am. Chem. Soc.*, 112:1546.

Jones, C. W. et al. (1998) *Nature* 393:52

Kitagawa, S., R. Kitaura and S. Noro (2004) *Angew. Chem., Int. Ed.*, 43:2334.

Li, H., M. Eddaoudi, M. O'Keeffe and O. M. Yaghi (1999) "Design and synthesis of an exceptionally stable and highly porous metal-organic framework" *Nature*, 402:276.

Moulton, B. and M. J. Zaworotko (2001) "From Molecules to Crystal Engineering: Supramolecular Isomerism and Polymorphism in Network Solids" *Chem. Rev.*, 101:1629.

O'Keeffe, M. & Hyde, B. G. (1996) "Crystal structures, I. Patterns and symmetry" *Mineralogical Society of America*, Washington, D.C.

O'Keeffe, M., Eddaoudi, M., Li, H., Reineke, T. & Yaghi, O. M. (2000) "Frameworks for extended solids: geometrical design principles" *J. Solid State Chem.*, 152:3-20.

O'Keeffe, M., Brese, N. E. (1992) "Uninodal 4-Connected Nets I: Nets Without 3- or 4-Rings" *Acta Crystallogr.*, A48:663-669.

Ozin, G. A. (2000) "Panoscopic materials: synthesis over 'all' length scales" *Chem. Comm.*, pp. 419-432.

Paillaud, J. L. et al. (2004) *Science* 304:990.

Seo, J. S., D. Whang, H. Lee, S. I. Jun, J. Oh, Y. J. Jeon and K. Kim (2000) "A homochiral metal-organic porous material for enantioselective separation and catalysis" *Nature*, 404: 982.

Seidel, S. R. and Stang, P. J. (2002) "High-Symmetry Coordination Cages via Self-Assembly" *Acc. Chem. Res.*, 35:972.

Stein, A., Keller, S. W., Mallouk, T. E. (1993) "Turning down the heat: Design and mechanism in solid-state synthesis" *Science,* 259:1558-1564.

Takeda, N., K. Umemoto, K. Yamaguchi and M. Fujita (1999) "A nanometer-sized hexahedral coordination capsule assembled from 24 components" *Nature,* 398:794.

Yaghi, O. M., O'Keeffe, M., Kanatzidis, M. (2000) "Design of Solids from molecular Building Blocks: Golden Opportunities for Solid State Chemistry" *J. Solid State Chem.,* 152:1-2.

Yaghi, O. M., O'Keeffe, M., Ockwig, N. W., Chae, H. K., Eddaoudi, M., Kim J. (2003) "Reticular synthesis and the design of new materials" *Nature,* 423:705-714.

Yamamoto, K. et al. (2003) *Science* 300:470.

We claim:

1. A zeolite-like metal organic framework (ZMOF) comprising a plurality of molecular building blocks (MBB) having an $MX_nY_m$ cluster wherein M is a metal; X is N, O, or S; Y is N, O, or S; n is 2, 3, or 4; and m is 2, 3, or 4, wherein the ZMOF consists of rigid tetrahedral secondary building units and organic links with the commensurate geometry of an expanded porous zeolite-net-like metal-organic framework wherein the ZMOF is a rho-ZMOF, a sod-ZMOF, or a USF-ZMOF.

2. The ZMOF according to claim 1, wherein M is beryllium, zinc, cadmium, mercury, or any of the transition metals (in the periodic table scandium through copper, yttrium through silver, lanthanum through gold, and all known elements from actinium on).

3. The ZMOF according to claim 2, wherein M is zinc, copper, lanthanum, cadmium, nickel, iron, cobalt or indium.

4. The ZMOF according to claim 1, wherein the X is N; Y is O; and n is 4.

5. The ZMOF according to claim 1, wherein the MBB comprises a ligand having a chelating functionality and a bridging functionality being i) an aromatic ring structure comprising one or more nitrogen atoms and ii) one or more carboxylate groups located in the α-position relative to said nitrogen.

6. The ZMOF according to claim 1, wherein the metal of said MBB is locked into position through the formation of five-membered rings via N—, O— heterochelation to the metal.

7. The ZMOF according to claim 1, wherein guest and $H_2O$ molecules associated with synthesis of said ZMOF are removed.

8. The ZMOF according to claim 1, wherein the $MX_nY_m$ cluster comprises $MN_4O_2$, $MN_4O_4$, $MN_2O_2$, or $MN_2O_4$.

9. The ZMOF according to claim 1, wherein the ZMOF comprises a tetrahedral building unit (TBU) of $InN_4$.

10. A method for synthesizing a metal organic framework, said method comprising reacting a metal salt and a ligand having chelating and bridging functionality relative to the metal ion of said metal salt, in a suitable solvent, in the presence of a structure directing agent (SDA) and crystallizing the solution, wherein said metal organic framework comprises a plurality of molecular building blocks (MBB) having an $MX_nY_m$ cluster wherein M is a metal; X is N, O, or S; Y is N, O, or S; n is 2, 3, or 4; and m is 2, 3, or 4, and wherein the ZMOF consists of rigid tetrahedral secondary building units and organic links with the commensurate geometry of an expanded porous zeolite-net-like metal-organic framework wherein the ZMOF is a rho-ZMOF, a sod-ZMOF, or a USF-ZMOF.

11. The method according to claim 10, wherein said crystallizing step comprises heating said solution from about room temperature to about 200° C. for at least about 4 to 12 hours.

12. The method according to claim 10, wherein said metal salt is $M(NO_3)_x$ where x=2 or 3.

13. The method according to claim 10, wherein said SDA is 1,3,4,6,7,8-hexahydro-2H-pyrimido[1,2-α]pyrimidine (HPP), imidazole, 4,4'-trimethylenedipiperidine, or 1,2-diaminocyclohexane.

14. The method according to claim 10, wherein said crystallizing step comprises heating at about 80° C. to about 90° C. for at least 10 hours followed by heating at about 95° C. to about 110° C. for at least 12 hours.

15. The method according to claim 10, wherein said SDA is HPP and said crystallizing step comprises heating at about 85° C. for about 12 hours followed by heating at about 100° C. for about 14 hours.

16. The method according to claim 10, wherein said SDA is imidazole and said crystallizing step comprises heating at about 85° C. for about 12 hours followed by heating at about 105° C. for about 23 hours.

17. The method according to claim 10, wherein said ligand is selected from the group consisting of 1H-Imidazole-2-carboxylic acid, 1H-pyrrole-2,4-dicarboxylic acid, 1H-Imidazole-4-5-dicarboxylic acid, 2,7-Diaza-antracene-1,8-dicarboxylic acid, pyrimidine-4-6-dicarboxylic acid, pyridine-2,5,dicarboxylic acid, and 2,7-diaza-anthracene-3,6-dicarboxylic acid.

18. The method according to claim 10, wherein said metal of said metal salt has a minimum coordination number of six and a maximum of eight.

19. The method according to claim 10, wherein said metal of said metal salt is beryllium, zinc, cadmium, mercury, or any of the transition metals (in the periodic table scandium through copper, yttrium through silver, lanthanum through gold, and all known elements from actinium on).

20. The method according to claim 19, wherein said metal of said metal salt is zinc, copper, lanthanum, cadmium, nickel, iron, cobalt or indium.

21. The method according to claim 10, wherein the anion of said metal salt is selected from the group consisting of $F^-$, $Cl^-$, $Br^-$, $I^-$, $ClO^-$, $ClO_2^-$, $ClO_3^-$, $ClO_4^-$, $OH^-$, $HCO_2^-$, $NO_3^-$, $SO_4^{2-}$, $SO_3^{2-}$, $PO_4^-$, $CO_3^{2-}$, $PF_4^-$ and organic counterions.

22. The method according to claim 10, wherein said solvent is selected from the group consisting of N,N-dimethyl formamide (DMF), ethanol, 4,4'-trimethylenedipiperidine, and 1,2-diaminocyclohexane.

23. The method according to claim 22, wherein said solvent further comprises acetonitrile.

24. The method according to claim 10, wherein said solvent is made acidic.

25. A ZMOF produced by the method of claim 10.

26. The method according to claim 10, wherein said metal salt is $In(NO_3)_3$.

27. A zeolite-like metal organic framework (ZMOF), wherein said ZMOF is a USF-ZMOF and comprises the formula $In_{2.5}(C_5N_2O_4H_2)_5(C_6N_2H_{16})_{1.25}(DMF)_{12}(CH_3CN)_3(H_2O)_8$.

28. A zeolite-like metal organic framework (ZMOF), wherein said ZMOF is a rho-ZMOF and comprises the formula $In_{48}(C_5N_2O_4H_2)_{96}(C_7N_3H_{15})_{24}(DMF)_{36}(H_2O)_{192}$.

29. A zeolite-like metal organic framework (ZMOF), wherein said ZMOF is a sod-ZMOF and comprises the formula $In(C_5N_2O_4H_2)_2(C_3N_2H_5)(DMF)_4(CH_3CN)(H_2O)_4$.

* * * * *

UNITED STATES PATENT AND TRADEMARK OFFICE
CERTIFICATE OF CORRECTION

PATENT NO. : 8,415,493 B2
APPLICATION NO. : 11/410359
DATED : April 9, 2013
INVENTOR(S) : Mohamed Eddaoudi and Yunling Liu It is certified that error appears in the above-identified patent and that said Letters Patent is hereby corrected as shown below:

In the Specifications:

Column 3,
Line 49, "can viewed" should read --can be viewed--.
Line 53, "shows a the" should read --shows the--.

Column 7,
Line 37, "ClO$_4^{-,\ OH-}$," should read --ClO$_4^-$, OH$^-$,--.
Line 38, "PF$_4^{3-}$" and" should read --PF$_4^-$ and--.
Line 62, "(FIG. 10)" should read --(FIG. 10).--.

Column 8,
Line 41, "zeolites" should read --zeolites.--.

Column 11,
Lines 1-2, "thus possibility the increase" should read --thus possibly increase--.
Line 30, ""a", an" should read --"a", "an",--.

Column 14,
Line 21, "In(NO$_3$)$_3$.2H$_2$O" should read --In(NO$_3$)$_3$ 2H$_2$O--.

Column 15,
Line 57, "is indicate" should read --is indicated--.

Column 16,
Line 37, "tetracyaiiotetraphenylmethane]" should read
--tetracyanotetraphenylmethane]--.
Line 39, "393:52" should read --393:52.--.

Signed and Sealed this
Twenty-seventh Day of August, 2013

Teresa Stanek Rea
*Acting Director of the United States Patent and Trademark Office*

CERTIFICATE OF CORRECTION (continued)
U.S. Pat. No. 8,415,493 B2

In the Claims:

Column 18, Claim 21
Line 44, "$PO_4^-$," should read --$PO_4^{3-}$,--.